US012721839B2

(12) United States Patent
Northrup et al.

(10) Patent No.: US 12,721,839 B2
(45) Date of Patent: Sep. 1, 2026

(54) SOFT CHEWABLE VETERINARY DOSAGE FORM

(71) Applicant: Intervet Inc., Madison, NJ (US)

(72) Inventors: Laura Ann Northrup, Edison, NJ (US); Keith Freehauf, Stockton, NJ (US); Niki Waldron, Vallejo, CA (US); Timothy Susko, Jersey City, NJ (US)

(73) Assignee: Intervet Inc., Rahway, NJ (US)

(*) Notice: Subject to any disclaimer, the term of this patent is extended or adjusted under 35 U.S.C. 154(b) by 1213 days.

(21) Appl. No.: 17/628,062

(22) PCT Filed: Jul. 21, 2020

(86) PCT No.: PCT/EP2020/070527
§ 371 (c)(1),
(2) Date: Jan. 18, 2022

(87) PCT Pub. No.: WO2021/013825
PCT Pub. Date: Jan. 28, 2021

(65) Prior Publication Data

US 2022/0323421 A1 Oct. 13, 2022

Related U.S. Application Data

(60) Provisional application No. 62/877,070, filed on Jul. 22, 2019.

(51) Int. Cl.

| | |
|---|---|
| ***A61K 31/365*** | (2006.01) |
| ***A61K 9/00*** | (2006.01) |
| ***A61K 9/20*** | (2006.01) |
| ***A61K 9/24*** | (2006.01) |
| ***A61K 31/4155*** | (2006.01) |
| ***A61K 31/42*** | (2006.01) |
| ***A61K 31/422*** | (2006.01) |
| ***A61K 45/06*** | (2006.01) |
| ***A61K 47/10*** | (2017.01) |
| ***A61K 47/22*** | (2006.01) |
| ***A61K 47/26*** | (2006.01) |
| ***A61K 47/36*** | (2006.01) |
| ***A61K 47/44*** | (2017.01) |
| ***A61P 33/14*** | (2006.01) |

(52) U.S. Cl.
CPC .......... *A61K 31/422* (2013.01); *A61K 9/0056* (2013.01); *A61K 31/365* (2013.01); *A61K 31/4155* (2013.01); *A61K 31/42* (2013.01); *A61K 47/10* (2013.01); *A61K 47/22* (2013.01); *A61K 47/26* (2013.01); *A61K 47/36* (2013.01); *A61K 47/44* (2013.01)

(58) Field of Classification Search
CPC .. A61K 31/422; A61K 9/0056; A61K 31/365; A61K 31/4155; A61K 31/42; A61K 47/10; A61K 47/22; A61K 47/26; A61K 47/36; A61K 47/44; A61K 9/2077; A61K 9/209; A61K 9/2095; A61K 45/06; A61P 33/14
USPC .......................................................... 424/410
See application file for complete search history.

(56) References Cited

U.S. PATENT DOCUMENTS

| | | | | |
|---|---|---|---|---|
| 3,950,360 | A | 4/1976 | Aoki et al. | |
| 4,134,973 | A | 1/1979 | Fisher | |
| 4,199,569 | A | 4/1980 | Chabala et al. | |
| 4,310,519 | A | 1/1982 | Albers-Schonberg et al. | |
| 4,427,663 | A | 1/1984 | Mrozik | |
| 4,468,390 | A | 8/1984 | Kitano | |
| 4,855,317 | A | 8/1989 | Gehret | |
| 4,859,657 | A | 8/1989 | O'Sullivan et al. | |
| 4,871,719 | A | 10/1989 | Maienfisch | |
| 4,874,749 | A | 10/1989 | Mrozik | |
| 4,920,148 | A | 4/1990 | Gehret | |
| 4,963,582 | A | 10/1990 | Sato et al. | |
| 4,973,711 | A | 11/1990 | Maienfisch | |
| 4,978,677 | A | 12/1990 | Gehret | |
| 5,055,596 | A | 10/1991 | Baker et al. | |
| 5,077,308 | A | 12/1991 | Blizzard | |
| 5,824,653 | A | 10/1998 | Beuvry et al. | |
| 8,628,794 | B2 * | 1/2014 | Isele | A61P 25/02 424/441 |
| 2006/0068020 | A1 * | 3/2006 | Cottrell | A61K 31/7048 424/490 |
| 2007/0066617 | A1 | 3/2007 | Mita et al. | |

(Continued)

FOREIGN PATENT DOCUMENTS

| | | | |
|---|---|---|---|
| CN | 1829448 | A | 9/2006 |
| CN | 104334159 | A | 2/2015 |
| EA | 011764 | B1 | 6/2009 |

(Continued)

OTHER PUBLICATIONS

Rodney, S. Y.; Riley, C. K.; Adebayo, A. S. The application of pregelatinized starch extracted from [*Artocarpus altilis* (Parkinson) Fosberg] (Breadfruit) as a direct compression binder in tablets. Tropical Agriculture, [s. I.], v. 93, p. 182-196, 2016. Disponível em: https://research.ebsco.com/linkpro (Year: 2016).*

(Continued)

*Primary Examiner* — Bethany P Barham
*Assistant Examiner* — Alexandra Nicole Isnor
(74) *Attorney, Agent, or Firm* — David J. Kerwick

(57) ABSTRACT

The present application relates to a soft chewable veterinary dosage form comprising a systemic parasiticide as well as a physiologically active macrocyclic lactone and to a method for preparing said soft chewable veterinary dosage form.

6 Claims, No Drawings

(56) References Cited

U.S. PATENT DOCUMENTS

2017/0100377 A1* 4/2017 Freehauf ................ A61K 31/35

FOREIGN PATENT DOCUMENTS

| | | | | |
|---|---|---|---|---|
| EP | 0007812 | A1 | 2/1980 | |
| EP | 0002916 | B1 | 12/1981 | |
| EP | 0677054 | B1 | 4/1998 | |
| GB | 1390336 | A | 4/1975 | |
| NZ | 237086 | A | 7/1993 | |
| WO | WO-2005013714 | A1 * | 2/2005 | ........... A23K 20/111 |
| WO | 2005063015 | A1 | 7/2005 | |
| WO | 2005085216 | A1 | 9/2005 | |
| WO | 2007079162 | A1 | 7/2007 | |
| WO | 2009002809 | A2 | 12/2008 | |
| WO | 2009003075 | A1 | 12/2008 | |
| WO | 2009024541 | A2 | 2/2009 | |
| WO | 2009080250 | A2 | 7/2009 | |
| WO | 2010070068 | A2 | 6/2010 | |
| WO | 2010079077 | A1 | 7/2010 | |
| WO | 2011075591 | A1 | 6/2011 | |
| WO | 2011124998 | A1 | 10/2011 | |
| WO | 2013119442 | A1 | 8/2013 | |
| WO | 2013150052 | A1 | 10/2013 | |
| WO | 2013150055 | | 10/2013 | |
| WO | 2014079825 | A1 | 5/2014 | |
| WO | 2015086551 | A1 | 6/2015 | |
| WO | 2019091940 | A1 | 5/2019 | |

OTHER PUBLICATIONS

Fankhauser, Rebecca et al., Efficacy of oral afoxolaner plus milbemycin oxime chewables against induced gastrointestinal nematode infections in dogs, Veterinary Parasitology, 225, 117-122, 2016.

Albers-Schonberg, G., Avermectins. Structure Determination, J. Am. Chem. Soc., 1981, 4216-4221, 103.

Davies, H. G., Avermectins and Milbemycins, Natural Product Reports, 1986, 87-121, 3.

Goudie, A.C., Doramectin—a potent novel endectocide, Veterinary Parasitology, 1993, 5-15, 49.

Mrozik, H., Synthesis of Milbemycins from Avermectins, Tetrahedron Letters, 1983, 5333-5336, vol. 24, No. 48.

Rabagliati, Franco M. et al., Preparation and characterization of some polymer/ pharmaceutical-based composites. Part. II ivermectin, Polym. Bull., 2018, 415-425, 75.

WHO Drug Information, International Nonproprietary Names for Pharmaceutical Substances (INN), Recommended INN: List 50, 2003, 267-285, vol. 17, No. 4.

* cited by examiner

SOFT CHEWABLE VETERINARY DOSAGE FORM

CROSS-REFERENCE TO RELATED APPLICATIONS

This application is a national stage entry under 35 U.S.C. § 371 of PCT/EP2020/070527 filed Jul. 21, 2020, which claims priority from and the benefit of U.S. Provisional Application No. 62/877,070, filed Jul. 22, 2019.

The present application relates to a soft chewable veterinary dosage form comprising a systemic parasiticide as well as a physiologically active macrocyclic lactone and to a method for preparing said soft chewable veterinary dosage form.

BACKGROUND OF THE INVENTION

A number of parasites can infest or infect domestic animals, especially companion animals such as cats and dogs. These pests and parasites are of great nuisance to both the animals and their owners.

Isoxazoline compounds are known in the art and these compounds and their use as parasiticides are described, for example, in US patent application US 2007/0066617, and international patent applications WO 2005/085216, WO 2007/079162, WO 2009/002809, WO 2009/024541, WO 2009/003075, WO 2009/080250, WO 2010/070068 and WO 2010/079077.

One known and convenient way of administering an isoxazoline compound to an animal is oral administration, by way of solid oral dosage forms. Compared to the common compressed tablet, soft chewable veterinary dosage forms are reported to have several advantages. For example, they may have a higher palatability for the treated animal, preferable texture and taste over a tablet and additionally they are better to chew and subsequently to swallow.

Soft chewable veterinary dosage forms comprising an isoxazoline compound are known in the art. For example, reference is made to WO 2013/119442 A1 and WO 2015/086551 A1

Further, macrocyclic lactones are known to act as very potent parasiticides especially as acaricides, anthelmintic agents and/or insecticides. Thus, they are also useful for treating ectoparasites as well as endoparasites of animals.

In view of the above and in order to enhance/improve the therapeutic effect of the above-described soft chewable dosage forms isoxazoline compounds, it would be desirable to have a solid oral dosage form further comprising one or more active agents from a different class such as the macrocyclic lactone(s) in order to broaden the spectrum of parasites controlled by the same dosage form.

However, in soft chewable dosage forms obtained from formulations as for example described in the above-mentioned WO 2013/119442 A1 and WO 20157086551 A1 to which one or more physiologically active macrocyclic lactones have been added, said active macrocyclic lactones are observed to form a significant amount of degradation product(s). In other words, when added to a common soft chewable veterinary formulation, macrocyclic lactone(s) are often not stable enough in the resulting dosage form to reliably provide an effective amount of such macrocyclic lactone compound.

Thus, there is still a need for soft chewable veterinary dosage forms comprising a combination of a systemically active parasiticidal compound, especially an agent from the group of isoxazoline compounds and a physiologically active macrocyclic lactone compound in which the stability of the physiologically active agents is ensured and the formation of degradation products of the physiologically active agents is advantageously reduced. This will advantageously allow a longer shelf life of the resulting product and allows storage of the product under more harsh conditions. Further, the stability of the physiologically active macrocyclic lactone should be improved without having a negative influence on the bioavailability of the physiologically active macrocyclic lactone. Another important consideration is that the macrocyclic lactone compound is generally present in the soft chewable veterinary dosage form in a very small amount. This creates a problem with content uniformity, i.e. to make sure that the macrocyclic lactone is uniformly distributed in the soft chew. Hence, it is an object of the present invention to overcome one or more of the drawbacks of the above-mentioned dosage forms.

In particular, it is an object of the present invention to provide a soft chewable veterinary dosage form inter alia containing a physiologically active macrocyclic lactone in a stabilized form such that its degradation is advantageously reduced or preferably even prevented.

SUMMARY OF THE INVENTION

The present invention has unexpectedly solved at least one of the above objectives by the provision of a new soft chewable veterinary dosage form.

Hence, in one aspect the subject of the present invention is directed to a soft chewable veterinary dosage form comprising (a) systemic insecticide and/or acaricide, (b) forming agent, (c) filler, (d) a liquid component (e) flavor, (f) an aggregate comprising (f1) one or more physiologically active macrocyclic lactone(s), (f2) binder, (f3) core material.

Another aspect of the current invention is a aggregate comprising one or more physiologically active macrocyclic lactone (f1), binder (f2), and core material (f3), wherein the core material (f3) is intimately associated with binder (f2) and physiologically active macrocyclic lactone (f1).

Another aspect of the current invention is a aggregate comprising one or more physiologically active macrocyclic lactone (f1), binder (f2), and core material (f3), wherein the aggregate is obtainable by melt processing of binder (f2) and active macrocyclic lactone (f1) with core material (f3).

Another aspect of the current invention is a method for preparing a soft chewable veterinary dosage form of the current invention comprising the steps:

(i) processing binder (f2) and physiologically active macrocyclic lactone (f1) with core material (f3) to obtain aggregate (f), (ii) blending the aggregate from step (i) with (a) systemic insecticide and/or acaricide, (b) forming agent, (c) filler, a liquid component (d)) and (e) flavor to obtain a dough, (iii) forming the dough from step (ii) to a soft chewable veterinary dosage form.

In one embodiment step (i) is conducted as melt processing.

In one embodiment step (i) comprises the following sub-steps:

(i1) heating binder (f2) to an elevated temperature T1 and subsequently adding physiologically active macrocyclic lactone (f1)

(i2) optionally heating core material (f3) to an elevated temperature T2

(i3) adding the core material (f3) from step (i2) to the mixture from step (i1) or vice versa to form aggregate (f).

Another aspect of the current invention is the use of a aggregate comprising one or more physiologically active macrocyclic lactone (f1), binder (f2) and core material (f3), wherein the core material (f3) is intimately associated with binder (f2) and physiologically active macrocyclic lactone (f1) in the preparation of a soft chewable veterinary dosage form.

Another aspect of the current invention is the use of a aggregate obtainable by melt processing binder (f2) and biologically active macrocyclic lactone (f1) with a core material (f3) in the preparation of a soft chewable veterinary dosage form.

DETAILED DESCRIPTION OF THE INVENTION

The present invention relates to a soft chewable veterinary dosage form comprising the above-mentioned components (a), (b), (c), (d), (e) and (f) comprising components (f1), (f2) and (f3). Specifically, in the present soft chewable veterinary dosage form the one or more physiologically active macrocyclic lactone(s) (f1) is present in form of a aggregate (f) comprising components (f1), (f2) and (f3).

"Soft chew" or "soft chewable veterinary dosage form" is intended to mean a product which is solid at room temperature and that can be soft to chew. Further, the product can be functionally chewy because the product has a plastic texture during the process of mastication in the mouth. Such soft chews have a softness that is similar to a cooked ground meat patty.

The present soft chewable veterinary dosage form comprises (a), (b), (c), (d), (e) and (f) comprising (f1), (f2) and (f3), which are further described below.

Component (a) is a systemic parasiticide, especially an insecticide and/or acaricide. Said component is administered orally in the soft chewable veterinary dosage form according to the invention. A systemic parasiticide can be referred to as an insecticide and/or acaricide or anthelmintic, which has an effect on the whole of the animal to be treated and not just on a single part of said animal.

In a preferred embodiment of the invention and/or embodiments thereof the systemic insecticide and/or acaricide (a) comprises an isoxazoline compound of the Formula (I)

Formula (I)

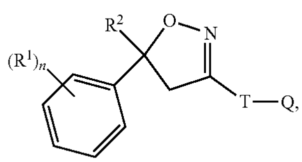

wherein $R^1$ is halogen, $CF_3$, $OCF_3$, CN, n is an integer from 0 up to and including 3, preferably 1, 2 or 3, $R^2$ is $C_1$-$C_3$-haloalkyl, preferably $CF_3$ or $CF_2Cl$, T is a 5 to 12 membered mono or bicyclic ring system, which is optionally substituted by one or more radicals Y, Y is methyl, halomethyl, halogen, CN, $NO_2$, NH2—C═S, or two adjacent radicals Y form together a chain, especially a three or four-membered chain;

Q is X—$NR^3R^4$, $NR^5$—$NR^6$—X—$R^3$, X—R3 or a 5-membered N-heteroaryl ring, which is optionally substituted by one or more radicals;

X is CH2, CH(CH3), CH(CN), CO, CS, $R^3$ is hydrogen, methyl, haloethyl, halopropyl, halobutyl, methoxymethyl, methoxy-ethyl, halomethoxymethyl, ethoxymethyl, haloethoxymethyl, propoxymethyl, ethylaminocarbonylmethyl, ethylaminocarbonylethyl, dimethoxyethyl, propynyl-aminocarbonylmethyl, N-phenyl-N-methyl-amino, haloethylaminocarbonyl-methyl, haloethylaminocarbonylethyl, tetrahydrofuryl, methylamino-carbonylmethyl, (N,N-dimethylamino)-carbonylmethyl, propylaminocarbonyl-methyl, cyclopropylaminocarbonylmethyl, propenylaminocarbonylmethyl, haloethylaminocarbonylcyclopropyl, alkylsulfanyl, alkylsufinalkyl, alkylsulfonalkyl, cycloalkyl $R^3$-1

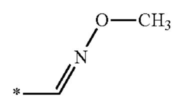

$R^3$-2

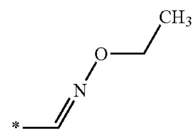

$R^3$-3

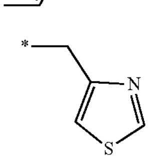

$R^3$-4

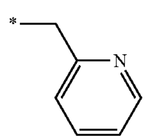

$R^3$-5

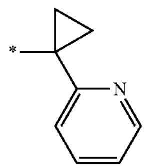

$R^3$-6

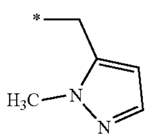

$R^3$-7

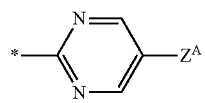

-continued $R^3$-8

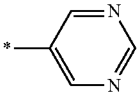

$R^3$-9

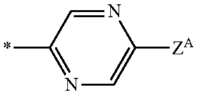

$R^3$-10

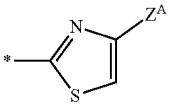

$R^3$-11

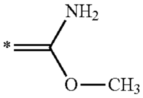

$R^3$-12

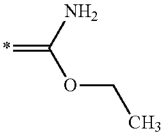

$R^3$-13

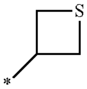

$R^3$-14

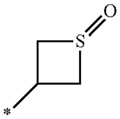

$R^3$-15

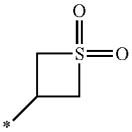

$R^3$-16

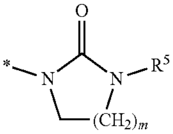

$R^3$-17

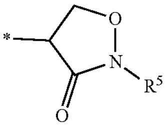

or $R^3$-18

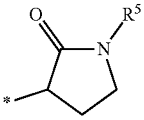

wherein $Z^A$ is hydrogen, halogen, cyano, halomethyl, preferably $CF_3$;

$R^4$ is hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethyl-aminocarbonylethyl;

$R^5$ is hydrogen, alkyl or haloalkyl;

$R^6$ is hydrogen, alkyl or haloalkyl;

or $R^3$ and $R^4$ together form a substituent selected from the group consisting of:

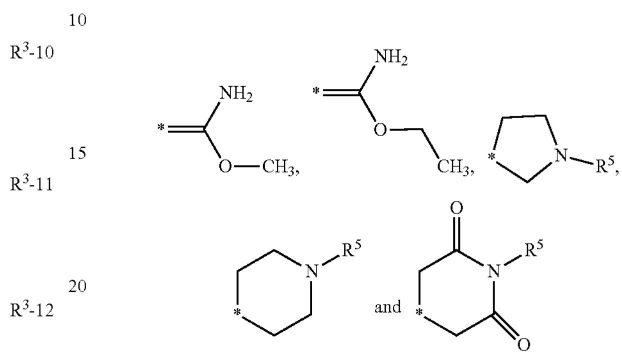

or a salt or solvate thereof.

In a preferred embodiment of the invention and/or embodiments thereof T is selected from

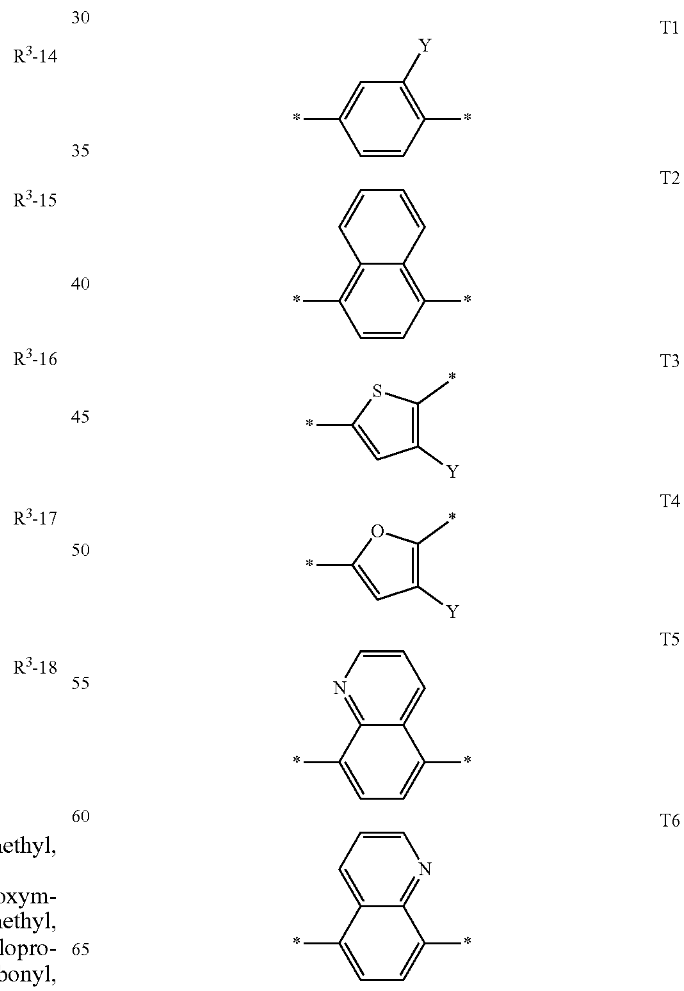

T1

T2

T3

T4

T5

T6

-continued
T7
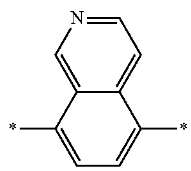
T8
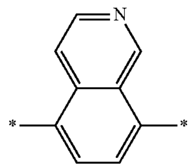
T9
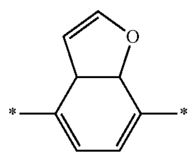
T10
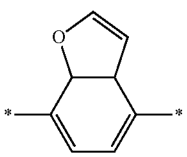
T11
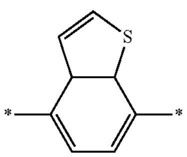
T12
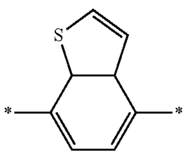
T13
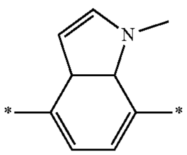
T14
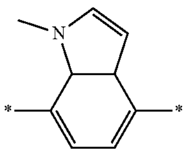
15
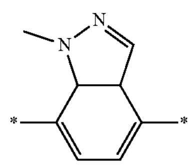
-continued
T16
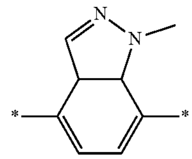
17
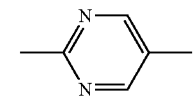
T18
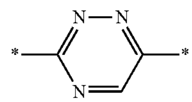
T19
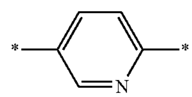
T20
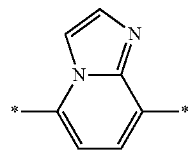
T21
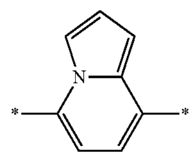
T22
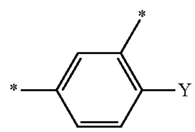
T23
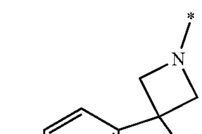
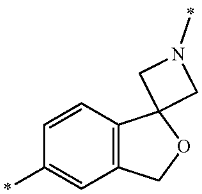
T24
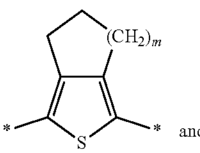
and
T25
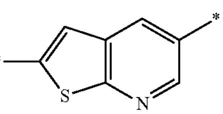
wherein in T-1, T-3 and T-4, the radical Y is preferably hydrogen, halogen, methyl, halomethyl, ethyl or haloethyl.
In a preferred embodiment of the invention and/or embodiments thereof Q in Formula (I) is selected from

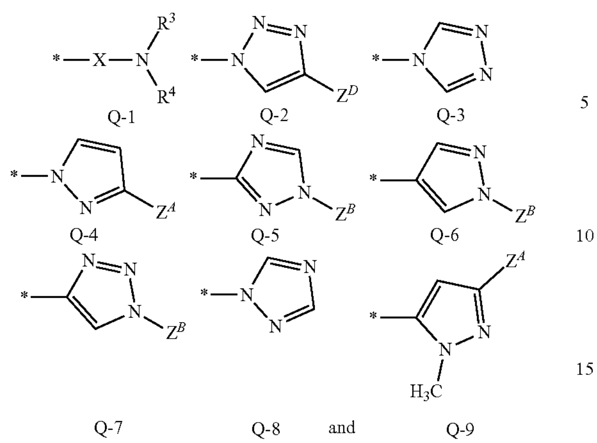

Q-1 Q-2 Q-3 Q-4 Q-5 Q-6 Q-7 Q-8 and Q-9 wherein $R^3$, $R^4$, X and $Z^A$ are as defined above and $Z^B$ is

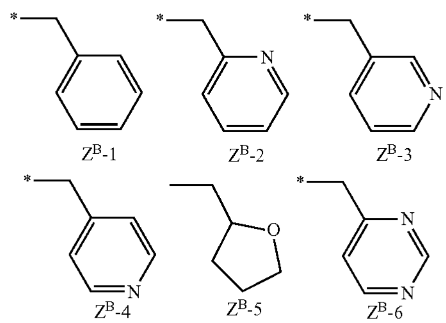

$Z^B$-1 $Z^B$-2 $Z^B$-3 $Z^B$-4 $Z^B$-5 $Z^B$-6

-continued

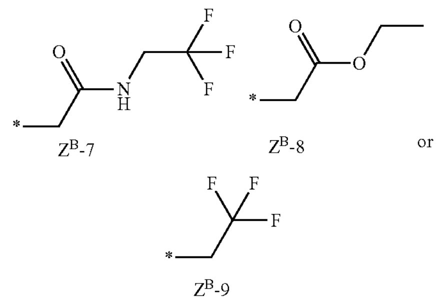

$Z^B$-7 $Z^B$-8 or $Z^B$-9

$Z^D$ is

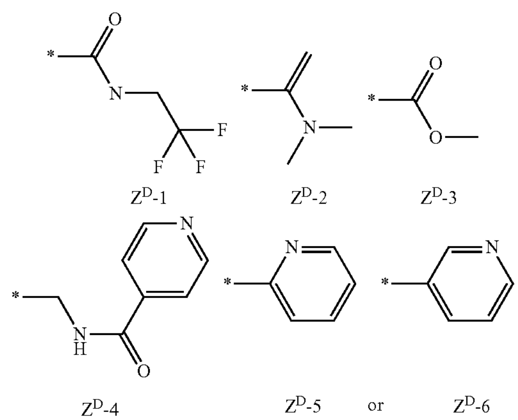

$Z^D$-1 $Z^D$-2 $Z^D$-3 $Z^D$-4 $Z^D$-5 or $Z^D$-6

Preferred compounds of Formula (I) are listed in Table 1:

TABLE 1

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-Cl, 5Cl | $CF_3$ | $CH_2C(O)NHCH_2CH_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CH_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CH_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | — | T-2 | — | Q-5 | $Z^B$-7 | |
| 3-Cl, 5Cl | $CF_3$ | — | — | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-Cl, 5Cl | $CF_3$ | $CH_2C(O)NHCH_2CC$ | H | T-3 | $CH_3$ | Q-1 | — | C(O) |
| 3-Cl, 5Cl | $CF_3$ | $CH_2C(O)NHCH_2CN$ | H | T-3 | $CH_3$ | Q-1 | — | C(O) |
| 3-Cl, 5Cl | $CF_3$ | $CH_2C(O)NHCH_2CH_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CH_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CH_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CH_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-Cl, 5-Cl | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CH_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |

TABLE 1-continued

| $(R^1)_n$ | $R^2$ | $R^3$ | $R^4$ | T | Y | Q | Z | X |
|---|---|---|---|---|---|---|---|---|
| 3-$CF_3$, 5-$CF_3$ | $CF_3$ | $CH_2C(O)NHCH_2CH_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CH_3$ | H | T-21 | — | Q-1 | — | C(O) |
| 3-Cl, 5-Cl | $CF_3$ | $CH_2CH_2SCH_3$ | H | T-21 | — | Q-1 | — | C(O) |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $CH_2C(O)NHCH_2CH_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

More preferred compounds of Formula (I) are listed in Table 2.

TABLE 2

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | — | T-2 | — | Q-5 | $Z^B$-7 | |
| 3-Cl, 5Cl | $CF_3$ | — | — | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-Cl, 5Cl | $CF_3$ | $CH_2C(O)NHCH_2CC$ | H | T-3 | $CH_3$ | Q-1 | — | C(O) |
| 3-Cl, 5Cl | $CF_3$ | $CH_2C(O)NHCH_2CN$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2CH_2SCH_3$ | H | T-21 | — | Q-1 | — | C(O) |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl 5-Cl | $F_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

In a particularly preferred embodiment of the invention and/or embodiments thereof the isoxazoline compound is represented by Formula (II)

Formula(II)

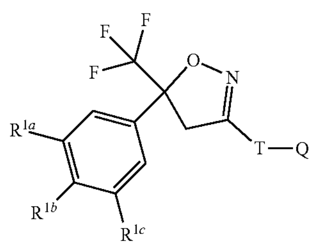

wherein $R^{1a}$, $R^{1b}$, $R^{1c}$ are independently from each other hydrogen, Cl or $CF_3$. Preferably $R^{1a}$ and $R^{1c}$ are Cl or $CF_3$ and $R^{1b}$ is hydrogen, T is

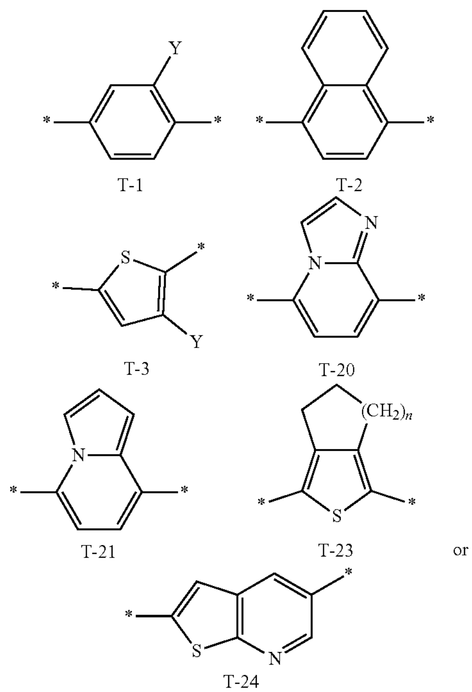

T-1, T-2, T-3, T-20, T-21, T-23 or T-24 wherein Y is methyl, bromine, Cl, F, CN or $C(S)NH_2$ and Q is as described above.

In another preferred embodiment of the invention and/or embodiments thereof $R^3$ is H and $R^4$ is —$CH_2$—C(O)—NH—$CH_2$—$CF_3$, —$CH_2$—C(O)—NH—$CH_2$—$CH_3$, —$CH_2$—CH2—CF3 or —$CH_2$—$CF_3$.

In another preferred embodiment of the invention and/or embodiments thereof the systemic insecticide and/or acaricide (a) is selected from fluralaner, afoxolaner, sarolaner, lotilaner and tigolaner.

In one preferred embodiment of the invention and/or embodiments thereof the systemic insecticide and/or acaricide (a) is 4-[5-(3,5-dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3). This compound is also known as fluralaner.

In one preferred embodiment of the invention and/or embodiments thereof the systemic insecticide and/or acaricide (a) is 4-[5-[3-chloro-5-(trifluoromethyl) phenyl]-4,5-dihydro-5-(trifluoromethyl)-3-isoxazolyl]-N-[2-oxo-2-[(2,2,2-trifluoroethyl) amino]ethyl]-1-naphthalenecarboxamide (CAS RN1093861-60-9). This compound is also known as a 4-[5-(5-chloro-a,a,a-trifluoro-m-tolyl)-4,5-dihydro-5-(trifluoromethyl)-1,2-oxazol-3y1]-N-[2-oxo-2-[(2,2,2-trifluoroethylamino]ethyl]naphthalene-1-or afoxolaner. Afoxolaner is for example disclosed in WO 2007/079162.

In one preferred embodiment of the invention and/or embodiments thereof the systemic insecticide and/or acaricide (a) 1-(5'-(5 -(3,5-dichloro-4-fluorophenyl)-5-(trifluoromethyl)-4,5-dihydroisoxazol-3-yl)-3'H-spiro[azetidine-3,1sobenzofuran]-1-yl)-2-(methylsulfonypethan-1-one, preferably 1-(5'-((5S)-(5-(3,5-dchloro-4-fluorophenyl)-5-(trifluoromethyl)-4,5-dihydro-soxazol-3-yl)-3'H-spiro[azetidine-3,1sobenzofuran]-1-yl)-2-(methylsulfonyl)ethan-1-one (CAS RN: 1398609-39-6). This compound is known as sarolaner.

In one preferred embodiment of the invention and/or embodiments thereof the systemic insecticide and/or acaricide (a) is 3-methyl-N-(2-oxo-2-((2,2,2-trifluoroethypamino)ethyl)-5-[5-(3,4,5-trichlorophenyl)-5-(trifluoromethyl)-4,5-dihydroisoxazol-3-yl]thiophene-2-carboxamide, preferably methyl-N-(2-oxo-2-2-trifluoroethyl)amino) ethyl)-5-[(5S)-5(3,4,5-trichloro-phenyl)-5-(trifluoromethyl)-4,5-dihydroisoxazol-3-yl]thiophene-2-carboxamide (CAS RN: 1369852-71-0). This compound is known as lotilaner.

In one preferred embodiment of the invention and/or embodiments thereof the systemic insecticide and/or acaricide (a) is 2-chloro-N-(1-cyanocyclopropyl)-5-[1-[2-methyl-5-(1,1,2,2,2-pentafluoroethyl)-4-(trifluoromethyl) pyrazol-3-yl]pyrazol-4-yl]benzamide (CAS RN 1621436) (tigolaner).

In one preferred embodiment of the invention and/or embodiments thereof the systemic insecticide and/or acaricide (a) is In another embodiment the compound of Formula (I) is (Z)-4-[5-(3,5-dichlorophenyl)-5-trifluoromethyl-4,5-dihydroisoxazol-3-yl]-N-[(methoxy-imino)methyl]-2-methylbenzamide (CASRN 928789-76-8).

In one preferred embodiment of the invention and/or embodiments thereof the systemic insecticide and/or acaricide (a) is 4-[5-(3,5-dichlorophenyl)-5-(trifluoromethyl)-4H-isoxazol-3-yl]-2-methyl-N-(thietan-3-yl) benzamide (CAS RN 1164267-94-0) that was disclosed in WO 2009/0080250.

In one preferred embodiment of the invention and/or embodiments thereof the systemic insecticide and/or acaricide (a) is 5-[5-(3,5-dDichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide 3-methyl-N-[2-oxo-2-[(2,2,2-trifluoroethyl)amino]ethyl]-2-thiophenecarboxamide (CAS RN 1231754-09-8) that was disclosed in WO 2010/070068.

Especially preferred is fluralaner (corresponding to 4-[5-(3,5-dichlorophenyl)-5-trifluoromethyl-4,5-dihydroisoxazol-3-yl]-2-methyl-N-[(2,2,2-trifluoro-ethylcarbamoyl)-methyl]-benzamide) as systemic insecticide and/or acaricide (a) which is represented by Formula (III)

Formula (III)

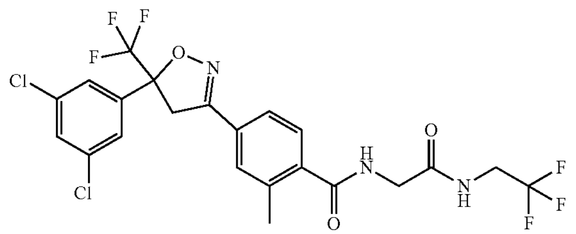

The isoxazoline compounds may exist in various isomeric forms. A reference to an isoxazoline compound always includes all possible isomeric forms of such a compound. Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound. In one embodiment the S-enantiomer of fluralaner of afoxolaner is present.

In line with the present application the terms "weight %" and "(w/w) %" can be used synonymously and designates weight/weight. As used herein, these terms represent the percentage by weight of an ingredient in the recipe of the dosage unit.

Component (b) is a forming agent. Component (b) binds the component together to influence the soft and plastic texture of the soft chewable veterinary dosage form. Further, said component (b) can enable the formation of a single soft chewable veterinary dosage form from a dough that stays intact and separate.

In one preferred embodiment of the invention and/or embodiments thereof the forming agent (b) is selected from polyethylene glycol, polypropylene glycol, polyethylene glycol-polypropylene glycol copolymer, microcrystalline wax, cetyl alcohol, polyvinylpyrrolidone, polyvinylpyrrolidone-polyvinylacetate copolymer, polysaccharides, hydroxypropyl methyl cellulose, poly(meth)acrylates, alkyl poly(meth)acrylates and mixtures thereof.

In one preferred embodiment of the invention and/or embodiments thereof the forming agent (b) is selected from polyethylene glycol, polypropylene glycol, polyethylene glycol-polypropylene glycol copolymer and mixtures thereof.

In one preferred embodiment of the invention and/or embodiments thereof the forming agent (b) is polyethylene glycol (PEG). Moreover, depending on the desired consistency of the soft chew, different molecular weight PEG may be utilized. Preferred are PEG components which are solid at room temperature and have a molecular weight higher than 600. Such PEGS preferably have a melting temperature between 30° C. and 80° C., preferably between 35° C. and 70° C., wherein the melting temperature is determined by means known to the skilled person.

In one preferred embodiment of the invention and/or embodiments thereof PEG 8000 may be utilized. The molecular weight of PEG 8000 may be higher or lower than 8000 g/mol, preferably between 6000 and 10000 g/mol.

In one preferred embodiment of the invention and/or embodiments thereof PEG 3350 or PEG 4000 may be utilized. The molecular weight of PEG 3350 or PEG 4000 may be higher or lower than 3350 g/mol, preferably between 2500 and 4500 g/mol, more preferred between 3000 and 4000 g/mol.

In one preferred embodiment of the invention and/or embodiments thereof the forming agent (b) is polyethylene glycol-polypropylene glycol copolymer (Poloxamer). Moreover, depending on the desired consistency of the soft chew, different molecular weight polyethylene glycol-polypropylene glycol copolymer may be utilized. In one preferred embodiment of the invention and/or embodiments thereof, Poloxamer 124 may be utilized.

Component (c) is a filler. Filler (c) can be an inorganic compound or an organic compound or a mixture thereof. In one preferred embodiment of the invention and/or embodiments thereof the filler (c) is selected from starch such as corn starch, sucrose, lactose, dextrin, dextrate, mannitol, sorbitol, isomalt, glucose, fructose, soy grits, soy protein fines microcrystalline cellulose, silicified microcrystalline cellulose, silica, titan dioxide, kaolin, bentonite, calcium phosphate and mixtures thereof. Preferably the filler (c) is selected from corn starch, sucrose, lactose, microcrystalline cellulose and mixtures thereof Component (d) is a liquid component. A liquid component is a component which is in a liquid state at 23° C. (room temperature) at a pressure of about 1 bar (about 1 000 hPa). The melting point of component (d) is preferably from −50° C. to 20° C. at a pressure of about 1 bar (about 1 000 hPa).

In one preferred embodiment of the invention and/or embodiments thereof the liquid component (d) is a solvent (d1) and/or a humectant (d2). The solvent is a liquid in which at least one of the active ingredients is at least partially soluble. The solvent (d1) is preferably an organic solvent e.g. Dimethylacetamide, N methyl pyrrolidone, 2-pyrrolidone, diethylene glycol monoethyl ether, ethyl lactate, ethylene monomethyl ether, glycofurol,) or liquid PEG, especially PEG 400 or combinations thereof.

A humectant (d2) is a substance, preferably a hygroscopic substance, to keep a product moist. A humectant can be considered as attracting and retaining the moisture in the air nearby via absorption, drawing the water vapor into or beneath the product's surface. Humectants can be molecules bearing several hydrophilic groups such as hydroxyl groups, amino groups, carboxyl groups, carboxylic acid ester groups and mixtures thereof, in particular hydroxyl groups and carboxylic acid ester groups. Examples of humectants are glycerol, caprylic/capric triglyceride, dicaprylate/dicarprate, propylene glycol, dicaprilate/dicarprate, medium chain triglycerides sold under the trademark Miglyol, especially Miglyol 812 or 814, vegetable oil, especially soybean oil, glycerol, butylene glycol, hexylene glycol, glyceryl triacetate or combinations thereof.

In one preferred embodiment of the invention and/or embodiments thereof the liquid component (d) is selected from caprylic/capric triglyceride, dicaprylate/dicarprate, propylene glycol dicaprilyte/dicarprate, medium chain triglycerides sold under the trademark Miglyol, especially Miglyol 812 or 814, vegetable oil, especially soybean oil, glycerol, 2-pyrrolidone, dimethyl acetamide, polyethylene glycol and mixtures thereof.

Component (e) is flavour. In one preferred embodiment of the invention and/or embodiments thereof the flavour (e) is selected from chicken flavour, pork flavour, beef flavour, ham flavour, fish flavour, vegetarian flavour, Chardex Hickory flavor, artificial flavour, sweet apple & molasses flavour and mixtures thereof, in particular, pork liver flavour.

Component (f) is an aggregate comprising (f1) physiologically active macrocyclic lactone, (f2) binder, and (f3) core material.

In line with the present application an aggregate is regarded as a number of distinct and different components, being grouped together and associated with each other in an embedding matrix. In other words, an aggregate is considered as an association of a number of distinct and different components that together form a matrix like mass. In a preferred embodiment the aggregate (f) is made of physiologically active macrocyclic lactone particles that are intimately associated with at least one binder and core material.

In one preferred embodiment of the invention and/or embodiments thereof the amount of the aggregate (f) comprised in the present soft chewable veterinary dosage form may be in the range of from 1 to 10 weight %, preferably 2 to 8 weight %, in particular 4 to 7 weight %.

In one preferred embodiment of the invention and/or embodiments thereof in aggregate (f) the core material (f3) is at least partially associated with binder (f2) and physiologically active macrocyclic lactone (f1). In another embodiment the core material (f3) is completely coated with binder (f2) and physiologically active macrocyclic lactone (f1).

Core material (f3) being intimately associated with binder (f2) and physiologically active macrocyclic lactone (f1) is obtainable by known methods. Examples of such methods are high-shear melt granulation and melt-processing that are known to the skilled person.

In one preferred embodiment of the invention and/or embodiments thereof the aggregate (f) is obtainable by melt processing binder (f2) and physiologically active macrocyclic lactone (f1) with core material (f3). In the course of such melt-processing the physiologically active macrocyclic lactone (f1) and the binder (f2) coat, preferably intimately associate, preferable cover, core material (f3). In other words, the core material (f3) can be regarded as embedded, preferably completely embedded in binder (f2) and physiologically active macrocyclic lactone (f1).

In one preferred embodiment of the invention and/or embodiments thereof the amount of the aggregate (f) comprised in the soft chewable veterinary dosage form may be in the range of from 1.5 to 7.5 weight %. In an alternative embodiment the amount of such a compound may be in the range of from 2 to 7 weight %. The preferred range is from 2.5 to 6.0 weight %.

In one preferred embodiment of the invention and/or embodiments thereof the melt processing binder (f2) and physiologically active macrocyclic lactone (f1) with core material (f3) comprises the following steps (i1) heating binder (f2) to an elevated temperature T1 and subsequently adding physiologically active macrocyclic lactone (f1)

(i2) optionally heating core material (f3) to an elevated temperature T2

(i3) adding the core material (f3) from step (i2) to the mixture from step (i1) to form aggregate (f).

In step (i1) binder (f2) is heated to an elevated temperature T1. An elevated temperature is referred to a temperature above 23° C. It is preferred that the heating conditions, in particular the elevated temperature T1, are selected such that the binder (f2) is melted or partially melted. It is preferred that the elevated temperature T1 is between 25° C. and 80° C., preferably between 30° and 75° C., in particular between 35° C. and 70° C. Subsequently, one or more physiologically active macrocyclic lactone(s) (f1) and optionally one or more physiological acceptable excipients as described below are/is added to the melted binder (f2). It is preferred that one or more physiologically active macrocyclic lactone(s) (f1) and optionally an antioxidant is added to the melted binder (f2). Step (i1) can preferably be carried out under mechanical treatment such as stirring. Preferably step (il) is carried out such that the one or more physiologically active macrocyclic lactone(s) (f1)) and optionally one or more physiological acceptable excipients, preferably an antioxidant, are dissolved, preferably completely dissolved, in the melted binder (f2). As far as physiologically acceptable excipients are concerned, the same applies as described below. In a preferred embodiment in step (i2) core material (f3) is heated to an elevated temperature T2. Alternatively, the core material is not heated before adding in step (i3). As far as elevated temperature T2 is concerned, substantially the same as described above with elevated temperature T1 applies. It is preferred that elevated temperature T2 substantially corresponds to elevated temperature T1. In other words, the difference between elevated temperature T1 and elevated temperature T2 is preferably less than 5° C.

Step (i1) and step (i2) can be carried in any order or simultaneously.

In step (i3) the core material (f3) from step (i2) is added to the mixture from step (il) or vice versa. Said step is preferably carried out such that a homogenous distribution of the core material (f3) throughout the binder (f2), the one or more physiologically active macrocyclic lactone(s) (f1) and the optionally one or more physiological acceptable excipient(s) is ensured. Said step can be preferably carried out under mechanical treatment such as stirring.

Subsequently the resulting mixture can preferably be cooled to room temperature (about 23° C.) and/or sieved through a mesh of the desired size, preferably 14 or 30 mesh, to from aggregate (f).

Component (f1) is one or more physiologically active macrocyclic lactone(s).

Physiologically active macrocyclic lactones (also referred to as or macrolides or macrocyclic lactones -ML) are organic molecules comprising a ring structure, wherein said molecules include a lactone group. Such a lactone group can also be considered as intramolecular carboxylic acid ester group. Macrocyclic lactones are often found in metabolic products in bacteria and fungi. Furthermore, in one embodiment, the soft chewable oral veterinary dosage forms of the invention may comprise a combination of two or more macrocyclic lactone active agents. For the avoidance of doubt, the term "macrocyclic lactone" as used herein includes both naturally occurring and synthetic or semi-synthetic macrocyclic lactones, especially parasiticidal avermectin and milbemycin compounds.

The macrocyclic lactones that may be used in the compositions of the invention include, but are not limited to, naturally produced avermectins (e.g. including the components designated as Ala, A1b, A2a, A1b, B1a, B1b, B2a and B2b) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin A3, milbemycin A4, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

The structure of the avermectins and milbemycins are closely related, e.g. by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of inter alia U.S. Pat. Nos. 4,468,390 and 5,824,653, EP 0 007 812 Al, U.K. patent specification 1 390 336, EP 0 002 916 and New Zealand patent No. 237 086. Naturally occurring milbemycins are described in U.S. Pat. No. 3,950,360 as well as in various references cited in "The Merck Index" $12^{th}$ ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and in EP 0 677 054.

In one preferred embodiment of the invention and/or embodiments thereof the one or more physiologically active macrocyclic lactone(s) (f1) is selected from abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin A3, milbemycin A4, milbemycin oxime, moxidectin, nemadectin and mixtures thereof.

In one preferred embodiment of the invention and/or embodiments thereof the one or more physiologically active macrocyclic lactone(s) (f1) is selected from ivermectin, abamectin, milbemycin oxime, moxidectin, doramectin, selamectin, eprinomectin, emamectin and mixtures thereof. More preferred as physiologically active macrocyclic lactone(s) (f1) is milbemycin oxime or moxidectin or alternatively ivermectin.

In one preferred embodiment of the invention and/or embodiments thereof the amount of the one or more physiologically active macrocyclic lactone(s) (f1) comprised in the aggregate (f) may be in the range of from 0.001 to 10 weight %, preferably 0.75 to 7.5 weight % of the aggregate, depending on the effective concentration that varies between the different macrocyclic lactone compounds.

In one preferred embodiment of the invention and/or embodiments thereof the one or more highly active physiologically active macrocyclic lactone(s) such as moxidectin (f1) comprised in the soft chewable veterinary dosage form may be in the range of from 0.0075 to 0.075 weight %. In an alternative embodiment the amount of such a compound may be in the range of from 0.01 to 0.07 weight %. The preferred range is from 0.0125 to 0.065 weight %.

In case that the physiologically active macrocyclic lactone (f1) is milbemycin oxime, the amount thereof comprised in the aggregate (f) may be in the range from 0.5 to 20 weight %, preferably about 1 weight %, about 2 weight %, about 3 weight %, about 4 weight, or about 5 weight % of the aggregate.

In one preferred embodiment of the invention and/or embodiments thereof the macrocyclic lactone(s) is ivermectin (f1) comprised in the soft chewable veterinary dosage form may be in the range of from 0.0075 to 0.075 weight %, preferably about 0.015weight %, about 0.0225 weight %, about 0.03 weight %, about 0.0375 weight %.

In case that the physiologically active macrocyclic lactone (f1) is moxidectin, the amount thereof comprised in the aggregate (f) may be in the range of from 0.25 to 2.5 weight %, preferably 0.5 to 2 weight %, in particular about 1 weight % of the aggregate.

In one preferred embodiment of the invention and/or embodiments thereof, the moxidectin (f1) comprised in the soft chewable veterinary dosage form may be in the range of from 0.0025 to 0.01875 weight %, preferably from 0.005 to 0.015 weight %, in particular 0.01 weight %.

Component (f2) is a binder. The binder (f2) is a substance which is capable being intimately associated with one or more physically active macrocyclic lactones(s) (f1) on a core material (f3), prefraby via melt-processing. The binder (f2) is a component that preferably has a melting temperature or a glass transition temperature ($T_g$), in case binder (f2) is a polymer, in the ranges from 25 to 100° C., preferably from 35 to 85° C., in particular from 40 to 70° C. The glass transition temperature is the temperature at which a polymer becomes brittle as it cools down and soft as it heats up. This means that hydrophilic polymers become soft at temperatures above the glass transition temperature ($T_g$) and become plastically deformable without breaking. The glass transition temperature or melting point are determined using methods known in the art.

In one preferred embodiment of the invention and/or embodiments thereof the binder (f2) is selected from polyethylene glycol, polypropylene glycol, polyethylene glycol-polypropylene glycol copolymer, microcrystalline wax, glycerol monostearate, glycerol tristearate, hydrogenated castor oil, polyethylene glycol glycerol hydroxystearate, polysaccharides, polyvinylpyrrolidone, polyvinyl alcohol, poly(meth)acrylates, polyvinylpyrrolidone-polyacetate copolymer and mixtures thereof.

In one preferred embodiment of the invention and/or embodiments thereof the binder (f2) is selected from polyethylene glycol, polypropylene glycol, polyethylene glycol-polypropylene glycol copolymer, microcrystalline wax, glycerol monostearate, hydrogenated castor oil, polyethylene glycol glycerol hydroxystearate and mixtures thereof.

In one preferred embodiment of the invention and/or embodiments thereof the binder (f2) is a polyethylene glycol (PEG). Alternatively PEGs of different molecular weight can be used to account for various soft chew processing temperatures. For example, if the PEG used in the dough requires processing temperatures of ~40° C., then the PEG used in the aggregate should be above 40° C. to make sure it does not melt off during processing.

In one preferred embodiment of the invention and/or embodiments thereof PEG 8000 or PEG 4600 may be utilized. The molecular weight of PEG 8000 or PEG 4600 may be higher or lower.

The binder (f2) comprised in the aggregate (f) may be in the range of from 5 to 40 weight %, preferably 15 to 35 weight %, in particular about 25 weight % of the aggregate.

Component (f3) is core material. Said component can be used to form a core on which different materials can be associated. Core material can be an organic compound, an inorganic compound or a mixture thereof. Core material (f3) may fulfil one or preferably more of the following requirements: chemical inertness, non-hygroscopicity and easy processability.

In one preferred embodiment of the invention and/or embodiments thereof the core material (f3) is selected from microcrystalline cellulose, lactose, corncob granules, maltodextrin, silica, corn starch, sodium starch glycolate, silicified microcrystalline cellulose, kaolin, titan dioxide, bentonite and mixtures thereof.

In one preferred embodiment of the invention and/or embodiments thereof the core material (f3) is selected from microcrystalline cellulose, corncob granules, maltodextrin, silica, corn starch, sodium starch glycolate and mixtures thereof. Particularly preferred as core material (f3) is microcrystalline cellulose, in particular microcrystalline cellulose which is referred to as Avicel PH 102, however alternative grades of MCC can be also used.

In one preferred embodiment of the invention and/or embodiments thereof the core material (f3) comprised in the aggregate (f) may be in the range of from 50 to 90 weight %, preferably 60 to 85 weight %, in particular about 75 weight % of the aggregate.

In one preferred embodiment of the invention and/or embodiments thereof the physiologically active macrocyclic lactone (f1) is moxidectin, the binder (f2) is polyethylene glycol-polypropylene glycol copolymer and the core material (f3) is microcrystalline cellulose. As far as the amounts of components (f1), (f2) and (f3) are concerned the same applies as described above.

In one preferred embodiment of the invention and/or embodiments thereof the physiologically active macrocyclic lactone (f1) is milbemycin oxime, the binder (f2) is polyethylene glycol and the core material (f3) is microcrystalline cellulose. As far as the amounts of components (f1), (f2) and (f3) are concerned the same applies as described above.

In one preferred embodiment of the invention and/or embodiments thereof the physiologically active macrocyclic lactone (f1) is milbemycin oxime, the binder (f2) is glycerol monostearate and the core material (f3) is microcrystalline cellulose. As far as the amounts of components (f1), (f2) and (f3) are concerned the same applies as described above.

In one preferred embodiment of the invention and/or embodiments thereof the present soft chewable veterinary dosage form further comprises one or more physiologically active lactone and one or more physiologically acceptable excipients. Physiologically acceptable excipients are known in the art. For example, they are described in "Gennaro, Remington: The Science and Practice of Pharmacy" (20th Edition, 2000). All such physiologically acceptable excipients must be substantially pharmaceutically or veterinary pure and non-toxic in the amounts employed and must be compatible with the active ingredients.

In one preferred embodiment of the invention and/or embodiments thereof the physiological acceptable excipients are selected from antioxidants, buffers, sugar components, surfactants, lubricants, stabilizers, flow agents, disintegration agents and preservatives and mixtures thereof.

Another aspect of the present invention is an aggregate comprising one or more physiologically active macrocyclic lactone (f1), binder (f2) and core material (f3), wherein the core material (f3) is intimately associated or embedded with binder (f2) and physiologically active macrocyclic lactone (f1).

As far as components (f1), (f2) and (f3) are concerned, the same applies as described above regarding aggregate (f).

Another aspect of the present invention is an aggregate comprising one or more physiologically active macrocyclic lactone(s) (f1), binder (f2) and core material (f3), wherein the aggregate is obtainable by melt processing of binder (f2) and one or more physiologically active macrocyclic lactone (s) (f1) with core material (f3).

As far as components (f1), (f2) and (f3) are concerned as well as the aggregate obtainable by melt processing of binder (f2) and one or more physiologically active macrocyclic lactone(s) (f1) with core material (f3), the same applies as described above regarding aggregate (f).

In one preferred embodiment of the invention and/or embodiments thereof the aggregate further comprises one or more pphysiologically acceptable excipients for which the same applies as described above.

Preferably, the aggregate further comprises an antioxidant, as described above, in particular butyl hydroxy toluene (BHT).

The aggregate can be included in a soft chewable veterinary dosage form. The soft chewable veterinary dosage form may further comprise components (a), (b), (c), (d) and (e). For these components (a), (b), (c), (d) and (e) the same applies as described above.

A further aspect of the present invention is a method for preparing a soft chewable veterinary dosage form according to the invention comprising the steps:

(i) processing binder (f2) and physiologically active macrocyclic lactone (f1) with core material (f3) to obtain aggregate (f), (ii) blending the aggregate from step (i) with (a) systemic insecticide and/or acaricide, (b) forming agent, (c) filler, a liquid component (d)) and (e) flavour to obtain a dough, (iii) forming the dough from step (ii) to a soft chewable veterinary dosage form.

The order of addition of the components (a), (b), (c), (d) and (e) and the aggregate for blending can be different. Step (i) of forming a aggregate (f), in which the core material (f3) is preferably intimately associated or embedded, more preferably completely covered, with binder (f2) and one or more physiologically active macrocyclic lactone(s) (f1) can be carried out by any known method or granulation method. As far as the methods are concerned, the same applies as described above.

In one preferred embodiment of the invention and/or embodiments thereof the aggregate (f) in step (i) is carried out such that one or more physiologically active macrocyclic lactone(s) (f1) and the binder (f2) cover, preferably completely embed, core material (f3). In other words, the core material (f3) can be regarded as embedded, preferably completely embedded, in binder (f2) and physiologically active macrocyclic lactone (f1).

In one preferred embodiment of the invention and/or embodiments thereof step (i) is conducted as melt processing.

In one preferred embodiment of the invention and/or embodiments thereof step (i) comprises the following steps (i1) heating binder (f2) to an elevated temperature T1 and subsequently adding one or more physiologically active macrocyclic lactone(s) (f1)

(i2) optionally heating core material (f3) to an elevated temperature T2

(i3) adding the core material (f3) from step (i2) to the mixture from step (i1) or vice versa to form aggregate (f).

As far as components (f1), (f2) and (f3) as well as steps (i1), (i2) and (i3) are concerned, the same applies as described above.

Step (ii) of blending the aggregate from step (i) with (a) systemic insecticide and/or acaricide, (b) forming agent, (c) filler, a liquid component (d)) and (e) flavour to obtain a dough can be carried out with methods known to the skilled person.

In one preferred embodiment of the invention and/or embodiments thereof step (ii) comprises the following sub-steps:

(ii1) blending systemic insecticide and/or acaricide (a), filler (c), flavour (e) and optionally one or more further solid physiologically acceptable excipients and aggregate (f)

(ii2) adding liquid component (d) and one or more further liquid physiologically acceptable excipients to the mixture from step (ii1)

(iii3) melting the forming agent (b)

(iii4) adding the molten forming agent (b) to the mixture of step (ii2) or vice versa to obtain a dough.

In step (iil) systemic insecticide and/or acaricide (a), filler (c), flavour (e) and optionally one or more further physiologically acceptable solid excipient(s) and aggregate (f) are blended. As far as these components are concerned, the same applies as described above. Blending is preferably carried out such that a homogenous mixture is obtained. It is preferred that blending according to step (iil) is carried out under mechanical treatment such as stirring.

In step (ii2) the liquid component (d) and optionally one or more further physiologically acceptable liquid excipient (s) to the mixture from step (ii1) are added. Preferably step (ii2) is carried out under blending. It is preferred that blending according to step (ii2) is carried out under mechanical treatment such as stirring.

Step (ii3) comprises melting, preferably completely melting, of the forming agent (d). Melting the forming agent is carried out at a temperature that is preferably in the range of the melting or glass transition temperature of the forming agent and a temperature that is higher than the melting or glass transition temperature of the forming agent, but preferably not more than about 30° higher than the melting or glass transition temperature of the forming agent. Step (iii3) is preferably carried out under blending. It is preferred that blending according to step (ii3) is carried out under mechanical treatment such as stirring.

The formation of the mixture according to step (ii2) and step (ii3) of melting the forming agent (d) can be carried in any order or simultaneously.

In step (ii4) the molten, preferably completely molten, forming agent (d) from step (iii3) is added to the mixture of step (ii2) or vice versa to obtain a dough. It is preferred that the molten, preferably completely molten, forming agent (d) is added to the mixture of step (ii2). This is preferably carried out under a mechanical treatment such as stirring. Further, it is preferred that the mixture of the molten forming agent (d) from step (iii3) and the mixture from step (ii2) is blended such that a dough, preferably a homogenous dough, is obtained.

In step (iii) a soft chewable veterinary dosage form is formed from the dough from step (ii). This can be carried out by utilizing any soft chew-forming machine known in the art such as the MFT 0100 Molding Machine (Kruger &Salecker) or the Formax F6™ (Formax Corporation). Alternatively, the soft chewable veterinary dosage form may be formed by other means known in the art. For example, the soft chewable veterinary dosage form may be formed by hand.

Another aspect of the present invention is the use of an aggregate comprising one or more physiologically active macrocyclic lactone(s) (f1), binder (f2) and core material (f3), wherein the core material (f3) is intimately associated with binder (f2) and physiologically active macrocyclic lactone (f1) in the formulation of a soft chewable dosage form.

In an alternate embodiment the invention as described above is applied in a compressed tablet dosage form.

Another aspect of the present invention is an aggregate comprising one or more physiologically active macrocyclic lactone(s) (f1), binder (f2) and core material (f3), wherein the aggregate is obtainable by melt processing of binder (f2) and one or more physiologically active macrocyclic lactone(s) (f1) with core material (f3).

As far as the components (f1), (f2) and (f3) are concerned as well as the core material (f3) being covered with binder (f2) and one or more physiologically active macrocyclic lactone (f1), the same applies as described above with aggregate (f).

Preferably, the aggregate further comprises an antioxidant, in particular butyl hydroxy toluene (BHT).

The aggregate can be further comprised in a soft chewable veterinary dosage form. The dosage form may further comprise components (a), (b), (c), (d) and (e). For these components (a), (b), (c), (d) and (e) the same applies as described above.

In general, the soft chewable veterinary dosage form according to the invention will contain an effective amount of the isoxazoline compounds of Formula (I) as defined above, meaning a non-toxic but sufficient amount to provide the desired control effect.

The soft chewable veterinary dosage form may be formulated to contain an amount of the systemic insecticide and/or acaricide and/or one or more physiologically active macrocyclic lactone(s) adjusted to animals in a specific weight range. The animals may receive a dosage of the dosage form according to the invention every 2, 3, 4, 5 or 6 months or receive a monthly, weekly or daily dosage.

One aspect of the invention is the use of an aggregate comprising one or more physiologically active macrocyclic lactone (f1), binder (f2) and core material (f3), wherein the core material (f3) is intimately associated with binder (f2) and physiologically active macrocyclic lactone (f1) in the preparation of a soft chewable veterinary dosage form.

Another aspect is the use of an aggregate obtainable by melt processing binder (f2) and biologically active macrocyclic lactone (f1) with a core material (f3) in the preparation of a soft chewable veterinary dosage form.

EXAMPLES

Example 1: Preparation of Aggregates Comprising a Macrocyclic Lactone

The components contained in the aggregates containing milbemycin oxime as macrocyclic lactone (f1) are described in aggregates 1(1)-1 to 1(19). The ones for the aggregates containing moxidectin as macrocyclic lactone (f1) are described in aggregate 1(20) to 1(37).

These Examples were prepared by following general procedure.

The binder (or combination of binders) (f2) was melted in a jacketed vessel until transparent.

The macrocyclic lactone and anti-oxidant (if present) were then added to the melted binder and dissolved at elevated temperature with mixing as needed. During this step, the core material (or combination of core material) was preheated to a temperature close to that of the melted binder.

Once the macrocyclic lactone had been fully dissolved, the core material was added to the binder/ macrocyclic lactone solution with constant mixing to ensure homogenous distribution of the core material throughout the binder.

Once cooled to ambient temperature, the obtained product was sieved through a mesh of the desired size (i.e. 14 mesh).

In the tables describing the aggregate the abbreviation “QS” (meaning “Quantum sufficit”) indicated that the amount of corresponding component may be adjusted to bring the composition to 100 weight %.

Aggregate 1(1)

| Ingredient | %(w/w) |
|---|---|
| Milbemycin Oxime | 5.0 |
| BHT | 0.1 |
| PEG 8000 | 25.0 |
| Avicel PH-102 | 69.9 (Q.S.) |

Aggregate 1(2)

| Ingredient | %(w/w) |
|---|---|
| Milbemycin Oxime | 5.0 |
| BHT | 0.1 |
| Kolliwax GMS II | 25.0 |
| Avicel PH-102 | 69.9 (Q.S.) |

Aggregate 1(3)

| Ingredient | %(w/w) |
|---|---|
| Milbemycin Oxime | 5.0 |
| BHT | 0.1 |
| PEG 4600 | 25.0 |
| Avicel PH-102 | 69.9 (Q.S.) |

Aggregate 1(6)

| Ingredient | %(w/w) |
|---|---|
| Milbemycin Oxime | 1.0 |
| BHT | 0.1 |
| Poloxamer 407 | 24.0 |
| Avicel PH-102 | 74.9 (Q.S.) |

Aggregate 1(4)

| Ingredient | %(w/w) |
|---|---|
| Milbemycin Oxime | 5.0 |
| BHT | 0.1 |
| Poloxamer 188 | 25.0 |
| Avicel PH-102 | 69.9 (Q.S.) |

Aggregate 1(7)

| Ingredient | %(w/w) |
|---|---|
| Milbemycin Oxime | 1.0 |
| BHT | 0.1 |
| Poloxamer 407 | 24.0 |
| Aeropearl 300 | 15.0 |
| Corn Starch | 59.9 (Q.S.) |

Aggregate 1(5)

| Ingredient | %(w/w) |
|---|---|
| Milbemycin Oxime | 1.0 |
| BHT | 0.1 |
| Poloxamer 407 | 24.0 |
| Corncob Granules | 74.9 (Q.S.) |

Aggregate 1(8)

| Ingredient | %(w/w) |
|---|---|
| Milbemycin Oxime | 1.0 |
| BHT | 0.1 |
| Poloxamer 407 | 24.0 |
| Maltodextrin M100 | 74.9 (Q.S.) |

Aggregate 1(9)

| Ingredient | %(w/w) |
|---|---|
| Milbemycin Oxime | 1.0 |
| BHT | 0.1 |
| Poloxamer 407 | 24.0 |
| Aeropearl 300 | 15.0 |
| Sodium Starch Glycolate, Type B | 59.9 (Q.S.) |

Aggregate 1(10)

| Ingredient | %(w/w) |
|---|---|
| Milbemycin Oxime | 1.0 |
| BHT | 0.1 |
| Kolliwax GMS II | 18.0 |
| Cremophor RH 40 | 6.0 |
| Corncob Granules | 74.9 (Q.S.) |

Aggregate 1(11)

| Ingredient | %(w/w) |
|---|---|
| Milbemycin Oxime | 1.0 |
| BHT | 0.1 |
| Kolliwax GMS II | 18.0 |
| Cremophor RH 40 | 6.0 |
| Avicel PH-102 | 74.9 (Q.S.) |

| Aggregate 1(12) | |
|---|---|
| Ingredient | %(w/w) |
| Milbemycin Oxime | 1.0 |
| BHT | 0.1 |
| Kolliwax GMS II | 18.0 |
| Cremophor RH 40 | 6.0 |
| Aeropearl 300 | 15.0 |
| Corn Starch | 59.9 (Q.S.) |

| Aggregate 1(13) | |
|---|---|
| Ingredient | %(w/w) |
| Milbemycin Oxime | 1.0 |
| BHT | 0.1 |
| Microcrystalline Wax | 24.0 |
| Maltodextrin M100 | 74.9 (Q.S.) |

| Aggregate 1(14) | |
|---|---|
| Ingredient | %(w/w) |
| Milbemycin Oxime | 1.0 |
| BHT | 0.1 |
| Kolliwax GMS II | 18.0 |
| Cremophor RH 40 | 6.0 |
| Aeropearl 300 | 15.0 |
| Sodium Starch Glycolate, Type B | 59.9 (Q.S.) |

| Aggregate 1(15) | |
|---|---|
| Ingredient | %(w/w) |
| Milbemycin Oxime | 1.0 |
| BHT | 0.1 |
| Microcrystalline Wax | 24.0 |
| Corncob Granules | 74.9 (Q.S.) |

| Aggregate 1(16) | |
|---|---|
| Ingredient | %(w/w) |
| Milbemycin Oxime | 1.0 |
| BHT | 0.1 |
| Microcrystalline Wax | 24.0 |
| Avicel PH-102 | 74.9 (Q.S.) |

| Aggregate 1(17) | |
|---|---|
| Ingredient | %(w/w) |
| Milbemycin Oxime | 1.0 |
| BHT | 0.1 |
| Microcrystalline Wax | 24.0 |
| Aeropearl 300 | 15.0 |
| Corn Starch | 59.9 (Q.S.) |

| Aggregate 1(18) | |
|---|---|
| Ingredient | %(w/w) |
| Milbemycin Oxime | 1.0 |
| BHT | 0.1 |
| Kolliwax GMS II | 18.0 |
| Cremophor RH 40 | 6.0 |
| Maltodextrin Ml 00 | 74.9 (Q.S.) |

| Aggregate 1(19) | |
|---|---|
| Ingredient | %(w/w) |
| Milbemycin Oxime | 1.0 |
| BHT | 0.1 |
| Microcrystalline Wax | 24.0 |
| Aeropearl 300 | 15.0 |
| Sodium Starch Glycolate, Type B | 59.9 (Q.S.) |

| Aggregate 1(20) | |
|---|---|
| Ingredient | %(w/w) |
| Moxidectin | 1.0 |
| BHT | 0.1 |
| Kolliwax GMS II | 25.0 |
| Avicel PH-102 | 73.9 (Q.S.) |

| Aggregate 1(21) | |
|---|---|
| Ingredient | %(w/w) |
| Moxidectin | 1.0 |
| BHT | 0.1 |
| Poloxamer 188 | 25.0 |
| Corncob Granules | 73.9 (Q.S.) |

| Aggregate 1(22) | |
|---|---|
| Ingredient | %(w/w) |
| Moxidectin | 1.0 |
| BHT | 0.1 |
| Poloxamer 188 | 25.0 |
| Avicel PH-102 | 73.9 (Q.S.) |

| Aggregate 1(23) | |
|---|---|
| Ingredient | %(w/w) |
| Moxidectin | 1.0 |
| BHT | 0.1 |
| Poloxamer 407 | 24.0 |
| Corncob Granules | 74.9 (Q.S.) |

| Aggregate 1(23 A) | |
|---|---|
| Ingredient | w/w % |
| Moxidectin | 1.0 |
| Citric Acid | 0.1 |
| Poloxamer 407 | 24.0 |
| Corncob Granules | 74.9 (Q.S.) |

| Aggregate 1(23B) | |
|---|---|
| Ingredient | w/w % |
| Moxidectin | 1.0 |
| BHT | 0.1 |
| Citric Acid | 0.1 |
| Poloxamer 407 | 24.0 |
| Corncob Granules | 74.8 (Q.S.) |

| Aggregate 1(24) | |
|---|---|
| Ingredient | %(w/w) |
| Moxidectin | 1.0 |
| BHT | 0.1 |
| Poloxamer 407 | 24.0 |
| Avicel PH-102 | 74.9 (Q.S.) |

| Aggregate 1(25) | |
|---|---|
| Ingredient | %(w/w) |
| Moxidectin | 1.0 |
| BHT | 0.1 |
| Poloxamer 407 | 24.0 |
| Aeropearl 300 | 15.0 |
| Corn Starch | 59.9 (Q.S.) |

| Aggregate 1(26) | |
|---|---|
| Ingredient | %(w/w) |
| Moxidectin | 1.0 |
| BHT | 0.1 |
| Poloxamer 407 | 24.0 |
| Maltodextrin M100 | 74.9 (Q.S.) |

| Aggregate 1(27) | |
|---|---|
| Ingredient | %(w/w) |
| Moxidectin | 1.0 |
| BHT | 0.1 |
| Poloxamer 407 | 24.0 |
| Aeropearl 300 | 15.0 |
| Sodium Starch Glycolate, Type B | 59.9 (Q.S.) |

| Aggregate 1(28) | |
|---|---|
| Ingredient | %(w/w) |
| Moxidectin | 1.0 |
| BHT | 0.1 |
| Kolliwax GMS II | 18.0 |
| Cremophor RH 40 | 6.0 |
| Corncob Granules | 74.9 (Q.S.) |

| Aggregate 1(29) | |
|---|---|
| Ingredient | %(w/w) |
| Moxidectin | 1.0 |
| BHT | 0.1 |
| Kolliwax GMS II | 18.0 |
| Cremophor RH 40 | 6.0 |
| Avicel PH-102 | 74.9 (Q.S.) |

| Aggregate 1(30) | |
|---|---|
| Ingredient | %(w/w) |
| Moxidectin | 1.0 |
| BHT | 0.1 |
| Kolliwax GMS II | 18.0 |
| Cremophor RH 40 | 6.0 |
| Aeropearl 300 | 15.0 |
| Corn Starch | 59.9 (Q.S.) |

| Aggregate 1(31) | |
|---|---|
| Ingredient | %(w/w) |
| Moxidectin | 1.0 |
| BHT | 0.1 |
| Kolliwax GMS II | 18.0 |
| Cremophor RH 40 | 6.0 |
| Maltodextrin M100 | 74.9 (Q.S.) |

| Aggregate 1(32) | |
|---|---|
| Ingredient | %(w/w) |
| Moxidectin | 1.0 |
| BHT | 0.1 |
| Kolliwax GMS II | 18.0 |
| Cremophor RH 40 | 6.0 |
| Aeropearl 300 | 15.0 |
| Sodium Starch Glycolate, Type B | 59.9 (Q.S.) |

| Aggregate 1(33) | |
|---|---|
| Ingredient | %(w/w) |
| Moxidectin | 1.0 |
| BHT | 0.1 |
| Microcrystalline Wax | 24.0 |
| Corncob Granules | 74.9 (Q.S.) |

| Aggregate 1(34) | |
|---|---|
| Ingredient | %(w/w) |
| Moxidectin | 1.0 |
| BHT | 0.1 |
| Microcrystalline Wax | 24.0 |
| Avicel PH-102 | 74.9 (Q.S.) |

| Aggregate 1(35) | |
|---|---|
| Ingredient | %(w/w) |
| Moxidectin | 1.0 |
| BHT | 0.1 |
| Microcrystalline Wax | 24.0 |
| Aeropearl 300 | 15.0 |
| Corn Starch | 59.9 (Q.S.) |

| Aggregate 1(36) | |
|---|---|
| Ingredient | % (w/w) |
| Moxidectin | 1.0 |
| BHT | 0.1 |
| Microcrystalline Wax | 24.0 |
| Maltodextrin M100 | 74.9 (Q.S.) |

| Aggregate 1(37) | |
|---|---|
| Ingredient | % (w/w) |
| Moxidectin | 1.0 |
| BHT | 0.1 |
| Microcrystalline Wax | 24.0 |
| Aeropearl 300 | 15.0 |
| Sodium Starch Glycolate, Type B | 59.9 (Q.S.) |

Example 2: Stability of Macrocyclic Lactone in Aggregate

Samples of selected aggregates from Example 1 containing milbemycin oxime were tested for stability. The aggregates were packaged in clear glass serum vials (type II) with bromobutyl stoppers and stored at 40° C./75% RH. The assay was measured using a UPLC method initially and at timepoints of 2 weeks and 3 months.

TABLE 3

| | Milbemycin Oxime Assay | | |
|---|---|---|---|
| Aggregates from Example 1 | Initial | 2 weeks | 3 months |
| Aggregate 1(1) | 108.0 | 103.4 | 109.1 |
| Aggregate 1(2)) | 100.4 | 102.6 | 106.2 |
| Aggregate 1(3) | 105.5 | 102.5 | 108.2 |

Additional samples of aggregates containing milbemycin oxime were tested for stability by placing in amber glass vials with screw caps at both 5° C. and 50° C., ambient humidity. The assay was measured using a UPLC method after 2 weeks.

TABLE 4

| | Milbemycin Oxime Assay | |
|---|---|---|
| Aggregates from Example 1 | 2 weeks at 5° C. | 2 weeks at 50° C. |
| Aggregate 1(5)) | 103.6 | 105.1 |
| Aggregate 1(6) | 100.5 | 102.8 |
| Aggregate 1(7) | 100.7 | 101.1 |
| Aggregate 1(8) | 102.4 | 102.2 |
| Aggregate 1(9) | 101.5 | 101.2 |

Samples of selected aggregates from Example 1 containing moxidectin were also tested for stability. The aggregate in Table 5 was packaged in amber scintillation vials and stored at ambient humidity at temperatures of 5° C., 25° C., 40° C., and/or 50° C. The assay was measured using a UPLC method initially, at 2 weeks, at 1 month, and/or at 3 months as noted in Table 5 and Table 6.

TABLE 5

| | Moxidectin Assay | | | | |
|---|---|---|---|---|---|
| Aggregate from Example 1 | Initial | 1 month at 25° C. | 1 month at 40° C. | 3 months at 25° C. | 3 months at 40° C. |
| Aggregate 1(22) | 103.7 | 102.8 | 103.8 | 103.8 | 109.6 |

TABLE 6

| | Moxidectin Assay | |
|---|---|---|
| Aggregates from Example 1 | 2 weeks at 5° C. | 2 weeks at 50° C. |
| Aggregate 1(25) | 101.6 | 95.5 |
| Aggregate 1(26) | 86.4 | 86.1 |
| Aggregate 1(27) | 94.3 | 94.3 |
| Aggregate 1(28) | 107.6 | 106.8 |
| Aggregate 1(29) | 107.7 | 107.0 |
| Aggregate 1(30) | 104.6 | 103.8 |
| Aggregate 1(31)) | 106.5 | 106.7 |
| Aggregate 1(32) | 110.3 | 109.1 |
| Aggregate 1(35) | 97.3 | 85.3 |
| Aggregate 1(37)) | 96.8 | 88.0 |

Example 3: Preparation of Soft Chewable Veterinary Dosage Forms (Including the Macrocyclic Lactone Aggregate of Example 1)

The aggregates described in Example 1 (aggregates 1(1) to 1(37)) were combined with various excipients and prepared by the following general procedure to create a soft chewable veterinary dosage form.

First, the dry excipients of the soft chew dosage form (including fluralaner, filler, flavour, surfactant, disintegrant, etc.) were combined and mixed until homogenous. At this time the aggregate including the macrocyclic lactone was added.

Once the dry excipients were mixed, the liquid excipients (including humectants and oils) were added and mixed. During this process the forming agent e.g. PEG (e.g. PEG 3350) was heated until molten.

The molten PEG was then added to the above described mixture to create a mixture with a "cook dough-like" appearance.

The mixture was then formed into individual chews of various sizes either manually, using a punch and die system with a stainless-steel die and a plastic punch such as a Formax F6, or by using a chew forming machine such as the MFT 0100 Moulding Machine from Krüger & Salecker.

Once dried, the chews were packaged into foil/foil pouches or blisters.

In the tables describing the soft chew veterinary dosage forms the abbreviation "QS" meaning "Quantun sufficit" indicated that the amount of corresponding component may be adjusted to bring the composition to 100% (w/w).

Dosage form 38

| Ingredient | % w/w |
|---|---|
| Aggregate 1(2) | 5.46 |
| Second Active | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Glycerol | 7.00 |
| Corn Starch | 13.73 (Q.S.) |

Dosage form 39

| Ingredient | % w/w |
|---|---|
| Aggregate 1(2) | 5.46 |
| Fluralaner | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Propylene Glycol | 3.00 |
| Corn Starch | 16.73 (Q.S.) |

Dosage form 40

| Ingredient | % w/w |
|---|---|
| Aggregate 1(2) | 5.46 |
| Fluralaner | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Poloxamer 124 | 3.00 |
| Corn Starch | 16.73 (Q.S.) |

Dosage form 41

| Ingredient | % w/w |
|---|---|
| Aggregate 1(2) | 5.46 |
| Fluralaner | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Triethyl Citrate | 3.00 |
| Corn Starch | 16.73 (Q.S.) |

Dosage form 42

| Ingredient | % w/w |
|---|---|
| Aggregate 1 (1) | 5.46 |
| Second Active | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Poloxamer 124 | 3.00 |
| Corn Starch | 16.73 (Q.S.) |

Dosage form 43

| Ingredient | % w/w |
|---|---|
| Aggregate 1(3) | 5.46 |
| Fluralaner | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl | 2.00 |

-continued

| Dosage form 43 | |
|---|---|
| Ingredient | % w/w |
| Sulfate | |
| Soybean oil | 12.00 |
| PEG 3350 | 20.00 |
| Poloxamer 124 | 3.00 |
| Corn Starch | 16.73 (Q.S.) |

| Dosage form 45 | |
|---|---|
| Ingredient | % w/w |
| Aggregate 1(3) | 5.46 |
| Fluralaner | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Glycerol | 7.00 |
| Corn Starch | 12.73 (Q.S.) |

| Dosage from 44 | |
|---|---|
| Ingredient | % w/w |
| Aggregate 1(1) | 5.46 |
| Fluralaner | 5.46 |
| Sodium Pamoate | 2.00 |
| BHT | 0.10 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Glycerol | 7.00 |
| Corn Starch | 12.73 (Q.S.) |

| Dosage form 46 | |
|---|---|
| Ingredient | % w/w |
| Aggregate 1(22) | 3.00 |
| Fluralaner | 15.00 |
| Pyrantel Pamoate | 8.67 |
| Sodium Starch Glycolate | 2.27 (Q.S.) |
| Sucrose | 6.00 |
| Pork Liver Flavor | 20.00 |
| Aspartame | 0.25 |
| Sodium Phosphate Tribasic | 1.85 |
| Sodium Lauryl Sulfate | 2.00 |
| Soybean oil | 12.00 |
| PEG 3350 | 20.00 |
| Glycerol | 9.00 |

-continued

| Dosage form 47 | |
|---|---|
| Ingredient | % w/w |
| Aggregate 1(22) | 3.00 |
| Fluralaner | 15.00 |
| Pyrantel Pamoate | 8.67 |
| Sodium Starch Glycolate | 11.27 (Q.S.) |
| Sucrose | 6.00 |
| Pork Liver Flavor | 20.00 |
| Aspartame | 0.25 |
| Sodium Phosphate Tribasic | 1.85 |
| Sodium Lauryl Sulfate | 2.00 |
| Soybean oil | 12.00 |
| PEG 8000 | 20.00 |

| Dosage form 48 | |
|---|---|
| Ingredient | % w/w |
| Aggregate 1(22) | 3.00 |
| Fluralaner | 15.00 |
| Pyrantel Pamoate | 8.67 |
| Sodium Starch Glycolate | 5.00 |
| Sucrose | 2.50 |
| Pork Liver Flavor | 20.00 |
| Aspartame | 0.25 |
| Sodium Lauryl Sulfate | 2.00 |
| Soybean oil | 13.50 |
| PEG 3350 | 17.30 |
| Glycerol | 3.00 |
| Corn Starch | 9.78 (Q.S.) |

| Dosage form 49 | |
|---|---|
| Ingredient | % w/w |
| Aggregate 1(22) | 3.00 |
| Fluralaner | 15.00 |
| Pyrantel Pamoate | 8.67 |
| Sodium Starch Glycolate | 5.00 |
| Sucrose | 2.50 |
| Pork Liver Flavor | 20.00 |
| Aspartame | 0.25 |
| Sodium Citrate | 1.00 |
| Sodium Lauryl Sulfate | 2.00 |
| Soybean oil | 13.50 |
| PEG 3350 | 17.30 |
| Glycerol | 3.00 |
| Corn Starch | 8.78 (Q.S.) |

| Dosage form 50 | |
|---|---|
| Ingredient | % w/w |
| Aggregate 1(23) | 3.00 |
| Fluralaner | 15.00 |
| Lactose | 8.70 (Q.S.) |
| Sodium Starch Glycolate | 5.00 |
| Pork Liver Flavor | 20.00 |
| Sodium Lauryl Sulfate | 2.00 |
| Soybean oil | 13.00 |
| PEG 8000 | 18.30 |
| Glycerol | 5.00 |
| Corn Starch | 10.00 |

| Dosage form 51 | |
|---|---|
| Ingredient | % w/w |
| Aggregate 1(23) | 3.00 |
| Fluralaner | 15.00 |
| Lactose | 8.70 (Q.S.) |
| Sodium Starch Glycolate | 5.00 |
| Pork Liver Flavor | 15.00 |
| Sodium Phosphate Dibasic | 0.35 |
| Sodium Lauryl Sulfate | 2.00 |
| Soybean oil | 13.65 |
| PEG 8000 | 18.30 |
| Glycerol | 5.00 |
| Corn Starch | 14.00 |

| Dosage from 52 | |
|---|---|
| Ingredient | % w/w |
| Aggregate 1(23) | 3.00 |
| Fluralaner | 15.00 |
| Pyrantel Pamoate | 8.67 |
| Sodium Starch Glycolate | 5.00 |
| Pork Liver Flavor | 15.00 |
| Sodium Phosphate Dibasic | 3.00 |
| Sodium Lauryl Sulfate | 2.00 |
| Soybean oil | 13.00 |
| PEG 8000 | 18.30 |
| Glycerol | 5.00 |
| Corn Starch | 12.03 (Q.S.) |

| Dosage form 53 | |
|---|---|
| Ingredient | % w/w |
| Aggregate 1(23) | 3.00 |
| Fluralaner | 15.00 |
| Lactose | 8.70 (Q.S.) |
| Sodium Starch Glycolate | 5.00 |
| Pork Liver Flavor | 15.00 |
| Sodium Citrate Dihydrate | 2.50 |
| Sodium Lauryl Sulfate | 2.00 |
| Soybean oil | 13.50 |
| PEG 8000 | 18.30 |
| Glycerol | 5.00 |
| Corn Starch | 12.00 |

| Dosage form 54 | |
|---|---|
| Ingredient | % w/w |
| Aggregate 1(23) | 3.00 |
| Fluralaner | 15.00 |
| Lactose | 8.70 (Q.S.) |
| Sodium Starch Glycolate | 5.00 |
| Pork Liver Flavor | 15.00 |
| EDTA Tetrasodium | 0.6 |
| Sodium Lauryl Sulfate | 2.00 |
| Soybean oil | 13.40 |
| PEG 8000 | 18.30 |
| Glycerol | 5.00 |
| Corn Starch | 14.00 |

| Dosage form 55 | |
|---|---|
| Ingredient | % w/w |
| Aggregate 1 (23) | 3.00 |
| Fluralaner | 15.00 |
| Pyrantel Pamoate | 8.67 |
| Sodium Starch Glycolate | 5.00 |
| Pork Liver Flavor | 15.00 |
| Sodium Phosphate Tribasic | 1.50 |
| Sodium Lauryl Sulfate | 2.00 |
| Soybean oil | 14.00 |
| PEG 8000 | 18.30 |
| Glycerol | 5.00 |
| Corn Starch | 12.53 (Q.S.) |

| Dosage form 56 | |
|---|---|
| Ingredient | % w/w |
| Aggregate 1(23) | 3.00 |
| Fluralaner | 15.00 |
| Pyrantel Pamoate | 8.67 |
| Sodium Starch Glycolate | 5.00 |
| Sucrose | 2.50 |
| Pork Liver Flavor | 20.00 |
| Aspartame | 0.25 |
| Sodium Lauryl Sulfate | 2.00 |
| Soybean oil | 13.50 |
| PEG 3350 | 17.30 |
| Glycerol | 3.00 |
| Corn Starch | 9.78 (Q.S.) |

| Dosage form 57 | |
|---|---|
| Ingredient | w/w % |
| Aggregate 1(23-A) | 3.00 |
| Fluralaner | 15.00 |
| Lactose | 23.70 (Q.S.) |
| Sodium Starch Glycolate | 5.00 |
| Pork Liver Flavor | 15.00 |
| Sodium Lauryl Sulfate | 2.00 |
| Soybean oil | 13.00 |
| PEG 8000 | 14.30 |
| Glycerol | 3.00 |
| Corn Starch | 6.00 |

| Dosage form 58 | |
|---|---|
| Ingredient | w/w % |
| Aggregate 1(23-B) | 3.00 |
| Fluralaner | 15.00 |
| Lactose | 23.70 (Q.S.) |
| Sodium Starch Glycolate | 5.00 |
| Pork Liver Flavor | 15.00 |
| Sodium Lauryl Sulfate | 2.00 |
| Soybean oil | 13.00 |
| PEG 8000 | 14.30 |
| Glycerol | 3.00 |
| Corn Starch | 6.00 |

Example 4: Stability of Soft Chewable Veterinary Dosage Forms

Samples of soft chewable veterinary dosage forms were tested for stability.

The soft chews were packaged in foil/foil pouches and stored at elevated temperature and humidity conditions, including 25° C./60% RH, 40° C./75% RH and/or 50° C./ambient humidity. The macrocyclic lactone assay was measured using a UPLC method initially and at timepoints of 2 weeks, 1 month, and/or 3 months as noted in Tables 7-10.

TABLE 7

| Soft chewable veterinary dosage forms from | Milbemycin Oxime Assay | | |
|---|---|---|---|
| Example 3 | Initial | 2 weeks at 50° C. | 1 month at 40° C. |
| Dosage form 38 | 98.0 | 93.7 | 92.0 |
| Dosage form 39 | 97.8 | 91.1 | 92.0 |
| Dosage form 40 | 97.9 | 95.1 | 96.4 |
| Dosage form 41 | 98.0 | 95.5 | NA |

TABLE 8

| Soft chewable veterinary dosage forms from | Milbemycin Oxime Assay | | |
|---|---|---|---|
| Example 3 | Initial | 2 weeks at 40° C. | 1 month at 50° C. |
| Dosage form 40 | 105.3 | 99.8 | 97.1 |
| Dosage form 42 | 105.2 | 101.3 | 99.2 |
| Dosage form 43 | 104.7 | 101.2 | 99.4 |
| Dosage form 38 | 102.3 | 94.0 | NA |
| Dosage form 44 | 101.5 | 93.5 | NA |
| Dosage form 45 | 99.7 | 91.3 | NA |

TABLE 9

| Soft chewable veterinary | Moxidectin Assay | | | | |
|---|---|---|---|---|---|
| dosage forms from Example 3 | Initial | 1 month at 40° C. | 1 month at 50° C. | 3 months at 25° C. | 3 months at 40° C. |
| Dosage form 46 | 96.2 | 91.5 | NA | 93.1 | 88.6 |
| Dosage form 47 | 102.2 | 98 | 96.6 | 98.8 | 98.2 |
| Dosage form 48 | 100.1 | 94.3 | 91.3 | 96.6 | 86.4 |

TABLE 10

| Soft chewable veterinary | Moxidectin Assay | | | |
|---|---|---|---|---|
| dosage forms from Example 3 | 2 weeks at 5° C. | 2 weeks at 50° C. | 1 month 40° C. | 1 month 50° C. |
| Dosage form 50 | 83.43 | 78.88 | 74.43 | 78.31 |
| Dosage form 51 | 83.35 | 81.84 | 78.83 | 75.79 |
| Dosage form 52 | 86.74 | 88.31 | 85.65 | 76.19 |
| Dosage form 53 | 85.13 | 82.68 | 78.63 | 73.58 |
| Dosage form 54 | 80.21 | 79.27 | 74.11 | 72.49 |
| Dosage form 55 | 82.89 | 80.45 | 79.01 | 73.82 |
| Dosage form 56 | 99.73 | 96.12 | NA | NA |
| Dosage form 57 | 86.85 | 83.55 | 80.13 | 79.86 |
| Dosage form 58 | 84.94 | 81.39 | 81.60 | 76.91 |

Example 5: Bioavailability of Soft Chewable Veterinary Dosage Form

The pharmacokinetic profile of milbemycin oxime was tested in a soft chewable veterinary dosage form formulation containing a aggregate 1(40).

The soft chewable veterinary dosage form was compared to a chewable veterinary dosage form (Reference dosage form 59) in which no aggregate was used and milbemycin was added directly to the formulation.

All formulations were administered orally to dogs randomly assigned to treatment groups with 8 animals in each. Individual body weights of each animal were used to manufacture tablets and chews to the target dose of 0.5 mg/ kg.

The milbemycin A4 oxime concentration in plasma was measured before treatment, at 30 minutes post treatment (0.02 days), and over several time points until no-longer detectable (approx. 21-28 days post treatment).

Average plasma concentrations are presented in Table 11. Table 12 presents the group averages of pharmacokinetic parameters for milbemycin A4 oxime.

| Reference dosage form 59 | |
|---|---|
| Ingredient | % w/w |
| Milbemycin Oxime | 1.00 |
| Fluralaner | 20.00 |
| Lactose | 48.40 (Q.S.) |
| Croscarmellose Sodium | 5.00 |
| Pork Liver Flavor | 20.00 |
| BHT | 0.1 |
| Povidone K30 | 5.00 |
| Magnesium Stearate | 0.5 |

TABLE 11

| Time Point (Days) | Average Milbemycin A4 concentration (ng/ml) for Reference dosage form 59 | Standard Deviation of Milbemycin A4 (ng/ml) for Reference dosage form 59 | Average Milbemycin A4 concentration (ng/ml) for dosage form 40 | Standard Deviation of Milbemycin A4 (ng/ml) for dosage form 40 |
|---|---|---|---|---|
| 0 | n.a. | n.a. | n.a. | n.a. |
| 0.02 | 22.41 | 22.18 | 22.85 | 10.77 |
| 0.04 | 107.68 | 60.70 | 99.72 | 42.46 |
| 0.08 | 191.33 | 50.81 | 173.12 | 57.01 |
| 0.17 | 137.58 | 38.86 | 135.67 | 31.91 |
| 0.33 | 71.83 | 23.05 | 76.93 | 18.58 |
| 1 | 40.28 | 11.53 | 40.90 | 7.79 |
| 2 | 27.90 | 8.78 | 27.18 | 4.29 |
| 3 | 22.08 | 7.30 | 19.55 | 3.91 |

TABLE 11-continued

| Time Point (Days) | Average Milbemycin A4 concentration (ng/ml) for Reference dosage form 59 | Standard Deviation of Milbemycin A4 (ng/ml) for Reference dosage form 59 | Average Milbemycin A4 concentration (ng/ml) for dosage form 40 | Standard Deviation of Milbemycin A4 (ng/ml) for dosage form 40 |
|---|---|---|---|---|
| 4 | 11.76 | 5.43 | 14.98 | 3.03 |
| 5 | 11.20 | 4.10 | 11.33 | 2.55 |
| 7 | 15.88 | 5.83 | 7.02 | 2.04 |
| 14 | 1.81 | 1.01 | 1.08 | 0.84 |
| 21 | 0.2 | 0.5 | n.a. | n.a. |
| 28 | n.a. | n.a. | n.a. | n.a. |

TABLE 12

| Parameter (unit) | Group Mean for Reference dosage form 59 | Standard Deviation for Reference dosage form 59 | Group Mean for dosage form 40 | Standard Deviation for dosage form 40 |
|---|---|---|---|---|
| $C^{max}$ (ng/ml) | 191.3 | 50.8 | 178.8 | 48.1 |
| Tmax (day) | 0.08 | 0.00 | 0.10 | 0.03 |
| AUC (ng*day/mL) | 250.4 | 82.7 | 205.9 | 48.5 |
| $AUC_{inf}$ (ng*day/mL) | 261.1 | 79.4 | 216.1 | 45.6 |
| $MRT_{last}$ (day) | 3.45 | 0.88 | 2.55 | 0.59 |
| $t_{1/2}$ (day) | 3.17 | 0.61 | 2.76 | 0.45 |

Example 6: Preparation of Soft Chewable Dosage Forms with Alternative Flavors Different flavors were investigated in dosage forms 60 to 63. Milbemycin is used in dosage form 60. Moxidectin is used in dosage forms 61-63.

Dosage form 60

| Ingredient | % w/w |
|---|---|
| aggregate 2 | 5.46 |
| Second Active | 5.46 |
| Sodium Pamoate | 2.00 |
| BHT | 0.10 |
| Sodium Starch Glycolate | 5.00 |
| Sucrose | 8.00 |
| Chardex Hickory Flavor | 2.00 |
| Aspartame | 0.25 |
| Sodium Lauryl Sulfate | 2.00 |
| Soybean oil | 12.00 |
| PEG 3350 | 20.00 |
| Glycerol | 6.00 |
| Corn Starch | 31.73 (Q.S.) |

Dosage form 61

| Ingredient | % w/w |
|---|---|
| aggregate 23 | 3.00 |
| Second Active | 15.00 |
| Lactose | 8.70 (Q.S.) |
| Sodium Starch Glycolate | 5.00 |
| Beef Flavor | 20.00 |
| Sodium Lauryl Sulfate | 2.00 |
| Soybean oil | 13.00 |
| PEG 8000 | 18.30 |
| Glycerol | 5.00 |
| Corn Starch | 10.00 |

Dosage form 62

| Ingredient | % w/w |
|---|---|
| Aggregate 1-23 | 3.00 |
| Second Active | 15.00 |
| Lactose | 8.70 (Q.S.) |
| Sodium Starch Glycolate | 5.00 |
| Sweet Apple & Molasses Flavor | 20.00 |
| Sodium Lauryl Sulfate | 2.00 |
| Soybean oil | 13.00 |
| PEG 8000 | 18.30 |
| Glycerol | 5.00 |
| Corn Starch | 10.00 |

Dosage form 63

| Ingredient | % w/w |
|---|---|
| aggregate 1-23 | 3.00 |
| Second Active | 15.00 |
| Lactose | 8.70 (Q.S.) |
| Sodium Starch Glycolate | 5.00 |
| Chardex Hickory Flavor | 2.00 |
| Toasted Soy Grits | 18.00 |
| Sodium Lauryl Sulfate | 2.00 |
| Soybean oil | 13.00 |
| PEG 8000 | 18.30 |
| Glycerol | 5.00 |
| Corn Starch | 10.00 |

Example 7: Stability of Soft Chewable Dosage forms with Different Flavors with Melt Granulation Aggregates Samples of soft chewable dosage forms containing the melt granulations aggregates were tested for stability.

The soft chew dosage forms were packaged in foil/foil pouches and stored at elevated temperature conditions, including 40° C. and 50° C./ambient humidity.

The macrocyclic lactone assay was measured using a UPLC method initially and at timepoints of 2 weeks and 1 month as noted in Tables 13 and 14.

TABLE 13

| Soft Chew dosage forms from Example 3 & 6 | | | |
|---|---|---|---|
| | Milbemycin Oxime Assay | | |
| | Initial | 2 weeks at 50° C. | 1 month at 40° C. |
| Dosage form 38 | 98.0 | 93.7 | 92.0 |
| Dosage form 55 | 101.2 | 93.8 | 94.1 |
| Dosage form 56 | 106.4 | NA | 100.9 |
| Dosage form 57 | 106.6 | NA | 99.8 |

TABLE 14

| Soft Chew Dosage forms from Example 6 | | | | |
|---|---|---|---|---|
| | Moxidectin Assay | | | |
| | 2 weeks at 5° C. | 2 weeks at 50° C. | 1 month 40° C. | 1 month 50° C. |
| Dosage form 58 | 80.5 | 74.8 | 76.1 | 65.6 |
| Dosage form 59 | 83.9 | 75.7 | 79.5 | 71.1 |
| Dosage form 60 | 85.8 | 85.1 | 81.5 | 82.3 |

Example 8: Preparation of Alternative Aggregates

The melt granulation aggregate of Ivermectin (described in aggregates 64 and 65) was prepared by the following general procedure described in Example 1 for all macrocyclic lactones.

aggregate 8 (64)

| Ingredient | Function | % (w/w) |
|---|---|---|
| Ivermectin | Active | 0.50 |
| BHT | Antioxidant | 0.1 |
| Poloxamer 188 | Binder | 25.0 |
| Avicel PH-102 | Carrier | 74.4 (Q.S.) |

aggregate 8 (65)

| Ingredient | Function | % (w/w) |
|---|---|---|
| Ivermectin | Active | 0.5 |
| BHT | Antioxidant | 0.1 |
| Kolliwax GMS II | Binder | 25.0 |
| Avicel PH-102 | Carrier | 74.4 (Q.S.) |

The melt granulation aggregates of macrocyclic lactones using 2 coats of binder was prepared by the following general procedure described.

All steps presented in Example 1 are followed, until the binder had been mixed with the carrier to form a granulation. Once the material was cooled, it was mixed with a secondary binder (also melted). The finalized granulation was sieved through a mesh of the desired size. The following examples use 2 binders to create a macrocyclic lactone aggregate premix, dosage form 66-70 use Milbemycin and dosage forms 71-79 use Moxidectin.

aggregate 8 (66)

| Ingredient | Function | % (w/w) |
|---|---|---|
| Milbemycin Oxime | Active | 1.00 |
| BHT | Antioxidant | 0.10 |
| Cremophor RH 40 | Binder | 2.82 |
| Microcrystalline Wax | Binder | 15.94 |
| Poloxamer 407 | Second Binder | 25.00 |
| Corncob Granules | Carrier | 55.14 (Q.S.) |

aggregate 8 (68)

| Ingredient | Function | % (w/w) |
|---|---|---|
| Milbemycin Oxime | Active | 1.00 |
| BHT | Antioxidant | 0.10 |
| Cremophor RH 40 | Binder | 2.82 |
| Microcrystalline Wax | Binder | 15.94 |
| Poloxamer 407 | Second Binder | 25.00 |
| Aeropearl 300 | Carrier | 11.25 |
| Corn Starch | Carrier | 43.89 (Q.S.) |

aggregate 8 (67)

| Ingredient | Function | % (w/w) |
|---|---|---|
| Milbemycin Oxime | Active | 1.00 |
| BHT | Antioxidant | 0.10 |
| Cremophor RH 40 | Binder | 2.82 |
| Microcrystalline Wax | Binder | 15.94 |
| Poloxamer 407 | Second Binder | 25.00 |
| Corncob Granules | Carrier | 55.14 (Q.S.) |

aggregate 8 (69)

| Ingredient | Function | % (w/w) |
|---|---|---|
| Milbemycin Oxime | Active | 1.00 |
| BHT | Antioxidant | 0.10 |
| Cremophor RH 40 | Binder | 2.82 |
| Microcrystalline Wax | Binder | 15.94 |
| Poloxamer 407 | Second Binder | 25.00 |
| Maltodextrin M100 | Carrier | 55.14 (Q.S.) |

| aggregate 8 (70) | | |
|---|---|---|
| Ingredient | Function | % (w/w) |
| Milbemycin Oxime | Active | 1.00 |
| BHT | Antioxidant | 0.10 |
| Cremophor RH 40 | Binder | 2.82 |
| Microcrystalline Wax | Binder | 15.94 |
| Poloxamer 407 | Second Binder | 25.00 |
| Aeropearl 300 | Carrier | 11.25 |
| Sodium Starch Glycolate, Type B | Carrier | 43.89 (Q.S.) |

| aggregate 8 (72) | | |
|---|---|---|
| Ingredient | Function | % w/w) |
| Moxidectin | Active | 1.00 |
| BHT | Antioxidant | 0.10 |
| Microcrystalline Wax | Binder | 18.75 |
| Poloxamer 407 | Second Binder | 25.00 |
| Aeropearl 300 | Carrier | 11.25 |
| Corn Starch | Carrier | 43.90 (Q.S.) |

| Aggregate 8 (73) | | |
|---|---|---|
| Ingredient | Function | % (w/w) |
| Moxidectin | Active | 1.00 |
| BHT | Antioxidant | 0.10 |
| Poloxamer 407 | Binder | 18.75 |
| Kolliwax GMS II | Second Binder | 25.00 |
| Corncob Granules | Carrier | 55.15 (Q.S.) |

| aggregate 8 (71) | | |
|---|---|---|
| Ingredient | Function | % (w/w) |
| Moxidectin | Active | 1.00 |
| BHT | Antioxidant | 0.10 |
| Microcrystalline Wax | Binder | 18.75 |
| Poloxamer 407 | Second Binder | 25.00 |
| Corncob Granules | Carrier | 55.15 (Q.S.) |

| aggregate 8 (74) | | |
|---|---|---|
| Ingredient | Function | % (w/w) |
| Moxidectin | Active | 1.00 |
| BHT | Antioxidant | 0.10 |
| Poloxamer 407 | Binder | 18.75 |
| Kolliwax GMS II | Second Binder | 25.00 |
| Avicel PH-102 | Carrier | 55.15 (QS.) |

| aggregate 8 (75) | | |
|---|---|---|
| Ingredient | Function | % (w/w) |
| Moxidectin | Active | 1.00 |
| BHT | Antioxidant | 0.10 |
| Poloxamer 407 | Binder | 18.75 |
| Kolliwax GMS II | Second Binder | 25.00 |
| Aeropearl 300 | Carrier | 11.25 |
| Corn Starch | Carrier | 43.90 (Q.S.) |

| aggregate 8 (78) | | |
|---|---|---|
| Ingredient | Function | % (w/w) |
| Moxidectin | Active | 1.00 |
| BHT | Antioxidant | 0.10 |
| Poloxamer | Binder | 18.75 |
| Poloxamer 407 | Second Binder | 25.00 |
| Corncob Granules | Carrier | 55.15 (Q.S.) |

| aggregate 8 (76) | | |
|---|---|---|
| Ingredient | Function | % (w/w) |
| Moxidectin | Active | 1.00 |
| BHT | Antioxidant | 0.10 |
| Poloxamer 407 | Binder | 18.75 |
| Kolliwax GMS II | Second Binder | 25.00 |
| Maltodextrin Ml00 | Carrier | 55.15 (Q.S.) |

| aggregate 8 (79) | | |
|---|---|---|
| Ingredient | Function | % (w/w) |
| Moxidectin | Active | 1.00 |
| BHT | Antioxidant | 0.10 |
| Poloxamer | Binder | 18.75 |
| Poloxamer 407 | Second Binder | 25.00 |
| Avicel PH-102 | Carrier | 55.15 (Q.S.) |

| aggregate 8 (77) | | |
|---|---|---|
| Ingredient | Function | % (w/w) |
| Moxidectin | Active | 1.00 |
| BHT | Antioxidant | 0.10 |
| Poloxamer 407 | Binder | 18.75 |
| Kolliwax GMS II | Second Binder | 25.00 |
| Aeropearl 300 | Carrier | 11.25 |
| Sodium Starch Glycolate, Type B | Carrier | 43.90 (Q.S.) |

Example 9: Stability of Alternative Melt Granulation Aggregates

Samples of melt granulation aggregates described in Example 8 containing Moxidectin were tested for stability by placing in amber glass vials with screw caps at both 5° C. and 50° C., ambient humidity. The assay was measured using a UPLC method after 2 weeks.

TABLE 15

| Melt Granulation | Moxidectin Assay | |
|---|---|---|
| aggregates from Example 8 | 2 weeks at 5° C. | 2 weeks at 50° C. |
| aggregate 8 (72) | 98.76 | 95.32 |
| aggregate 8 (73) | 101.26 | 99.49 |
| aggregate 8 (74) | 101.38 | 101.31 |
| aggregate 8 (75) | 101.14 | 99.8 |
| aggregate 8 (76) | 97.58 | 97.47 |
| Aggregate 8 (77) | 99.53 | 98.78 |

Example 10: Preparation and Stability of Soft Chew Dosage Forms with Aggregates Containing Ivermectin Soft chew dosage forms were manufactured as previously described in Example 3 but used aggregates with Ivermectin (aggregates 64 or 65).

| Dosage form 80 | |
|---|---|
| Ingredient | % w/w |
| aggregate 8(64) | 0.655 |
| Second Active | 5.46 |
| Pyrantel Pamoate | 7.89 |
| BHT | 0.001 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Glycerol | 9.00 |
| Corn Starch | 9.68 (Q.S.) |

| Dosage form 81 | |
|---|---|
| Ingredient | % w/w |
| aggregate 8(65) | 0.655 |
| Second Active | 5.46 |
| Pyrantel Pamoate | 7.89 |
| BHT | 0.001 |
| Sodium Starch Glycolate | 5.00 |
| Sucrose | 8.00 |
| Pork Liver Flavor | 20.00 |
| Aspartame | 0.25 |
| Sodium Lauryl Sulfate | 2.00 |
| Soybean oil | 12.00 |
| PEG 3350 | 20.00 |
| Glycerol | 9.00 |
| Corn Starch | 9.68 (Q.S.) |

TABLE 16

| | Ivermectin Assay | |
|---|---|---|
| Soft Chew dosage forms from Example 10 | Initial | 1 month at 50° C. |
| Dosage form 80 | 75.2 | 72.7 |
| Dosage form 81 | 87.6 | 81.0 |

The invention claimed is:

1. A Method for preparing a soft chewable veterinary dosage form comprising (a) fluralaner or a salt or solvate thereof;

(b) a forming agent polyethylene glycol (PEG) that has a melting temperature between 30° C. and 80° C., (c) a filler selected from starch such as corn starch, sucrose, lactose, dextrin, dextrate, mannitol, sorbitol, isomalt, glucose, fructose, soy grits, soy protein fines microcrystalline cellulose, silicified microcrystalline cellulose, silica, titan dioxide, kaolin, bentonite, calcium phosphate and mixtures thereof;

(d) a liquid component comprising caprylic/capric triglyceride, dicaprylate/dicarprate, propylene glycol dicaprilyte/dicarprate, medium chain triglycerides, vegetable oil, glycerol, 2-pyrrolidone, dimethyl acetamide, polyethylene glycol and mixtures thereof;

(e) one or more flavors, and (f) an aggregate comprising (f1) one or more physiologically active macrocyclic lactone(s), (f2) a binder (f3) a core material wherein the macrocyclic lactone is milbemycin oxime or moxidectin, the binder is polyethylene glycol and the core material is microcrystalline cellulose comprising the steps:

(i) processing the binder (f2) and the physiologically active macrocyclic lactone (f1) with the core material (f3) to obtain the aggregate (f), wherein step (i) comprises the following sub-steps (i1) melt processing by heating the binder (f2) to an elevated temperature T1 between 25° C. and 80° C. and subsequently adding the physiologically active macrocyclic lactone (f1)

(i2) adding the core material (f3) to the mixture from step (i1) or vice versa to form aggregate (f), (ii) blending the aggregate from step (i) with (a) fluralaner, (b) forming agent, (c) filler, (d) a liquid component and (e) flavor to obtain a dough, (iii) forming the dough from step (ii) to a soft chewable veterinary dosage form.

2. The method according to claim 1, wherein the flavor is selected from chicken flavor, pork flavor, beef flavor, ham flavor, fish flavor, vegetarian flavor, Chardex Hickory flavor, artificial flavor, sweet apple & molasses flavor and mixtures thereof.

3. The method according to claim 2, wherein the flavor is pork liver flavor.

4. The method according to claim 1, wherein the physiologically active macrocyclic lactone (f1) is milbemycin oxime.

5. The method of claim 1, wherein the forming agent b) is PEG with a molecular weight between 6000 and 10000 g/mol.

6. The method of claim 1, wherein in the course of the melt-processing in step (i1) the physiologically active macrocyclic lactone (f1) and the binder (f2) cover the core material (f3).

* * * * *